United States Patent
Wu et al.

(10) Patent No.: US 11,439,657 B2
(45) Date of Patent: Sep. 13, 2022

(54) CANCER STEM CELL GROWTH INHIBITOR USING MIRNA

(71) Applicant: CancerStem Tech Inc., Ibaraki (JP)

(72) Inventors: Xin Wu, Nishinomiya (JP); Masaki Mori, Toyonaka (JP); Hirofumi Yamamoto, Osaka (JP)

(73) Assignee: CancerStem Tech Inc., Ibaraki (JP)

( * ) Notice: Subject to any disclaimer, the term of this patent is extended or adjusted under 35 U.S.C. 154(b) by 0 days.

(21) Appl. No.: 16/498,986

(22) PCT Filed: Mar. 30, 2018

(86) PCT No.: PCT/JP2018/013560
§ 371 (c)(1),
(2) Date: Sep. 27, 2019

(87) PCT Pub. No.: WO2018/181877
PCT Pub. Date: Oct. 4, 2018

(65) Prior Publication Data
US 2021/0052627 A1    Feb. 25, 2021

(30) Foreign Application Priority Data

Mar. 30, 2017  (JP) .............................. JP2017-066599

(51) Int. Cl.
| | |
|---|---|
| *C07H 21/02* | (2006.01) |
| *C07H 21/04* | (2006.01) |
| *A61K 31/7105* | (2006.01) |
| *A61P 35/00* | (2006.01) |
| *C12N 15/113* | (2010.01) |
| *A61K 45/06* | (2006.01) |

(52) U.S. Cl.
CPC .......... *A61K 31/7105* (2013.01); *A61P 35/00* (2018.01); *C12N 15/113* (2013.01); *A61K 45/06* (2013.01); *C12N 2310/141* (2013.01)

(58) Field of Classification Search
CPC .................. C12N 15/113; C12N 2310/141
See application file for complete search history.

(56) References Cited

U.S. PATENT DOCUMENTS

| | | |
|---|---|---|
| 2010/0179213 A1 | 7/2010 | Patrawala et al. |
| 2015/0126579 A1 | 5/2015 | Pandolfi et al. |
| 2015/0267193 A1 | 9/2015 | Dasgupta |
| 2016/0145628 A1 | 5/2016 | Yerushalmi et al. |
| 2017/0073675 A1 | 3/2017 | Yamamoto et al. |

FOREIGN PATENT DOCUMENTS

| | | |
|---|---|---|
| JP | 2008-239596 A | 10/2008 |
| JP | 2014-515024 A | 6/2014 |
| KR | 2015-0096304 A | 8/2015 |
| WO | WO 2015-133521 A1 | 9/2015 |
| WO | WO 2018-018077 A1 | 2/2018 |

OTHER PUBLICATIONS

Ma et al. (Acta Biochim Biophys Sin, 2015, 47(8), 630-638).*
Chowdhury et al. (ResearchGate, 2015, pp. 1-5).*
Wu et al. (FEBS Letters, 589, 2015, 1911-1919).*
Wang et al. (Oncology Reports, 35, 2733-2742, 2016).*
International Search Report in International Application No. PCT/JP2018/013560, dated Jun. 19, 2018.
Japanese Office Action in Japanese Patent Application No. 2019-510231 dated Apr. 12, 2022.

* cited by examiner

*Primary Examiner* — Amy H Bowman
(74) *Attorney, Agent, or Firm* — Knobbe, Martens, Olson & Bear, LLP

(57) ABSTRACT

The purpose of the present invention is to provide a nucleic acid medication for cancer treatment, the medication being capable of suppressing the growth of cancer stem cells and thus effectively treating cancer. hsa-miR-136-5p, hsa-miR-3065-3p, hsa-miR-4727-5p, hsa-miR-378g, hsa-miR-181a-5p, hsa-miR-362-5p, and hsa-miR-608 have remarkably excellent growth inhibitory action on cancer stem cells and are thus useful as a nucleic acid medication for the treatment of various cancers.

5 Claims, 9 Drawing Sheets

Specification includes a Sequence Listing.

a b

CANCER STEM CELL GROWTH INHIBITOR USING MIRNA

TECHNICAL FIELD

The present invention relates to an agent for inhibiting proliferation of cancer stem cell. Specifically, the present invention relates to an agent for inhibiting proliferation of cancer stem cell, which can suppress cancer stem cell proliferation by a specific miRNA and thus allow for effective treatment of cancer.

REFERENCE TO SEQUENCE LISTING

A Sequence Listing submitted as an ASCII text file via EFS-Web is hereby incorporated by reference in accordance with 35 U.S.C. § 1.52(e). The name of the ASCII 15 text file for the Sequence Listing is 31408533_1.txt, the date of creation of the ASCII text file is Sep. 27, 2019, and the size of the ASCII text file is 2.90 KB.

BACKGROUND ART miRNA is a small RNA composed of 18-24 nucleotides and is widely present in eukaryotes. The existence of several thousand miRNAs has been revealed in humans. miRNA is an endogenously expressed short RNA, which has been first reported in 1993. An RNA called pri-miRNA having a loop structure is transcribed from DNA. The loop is cleaved by enzyme to make a pre-miRNA. This pre-miRNA is transported outside the nucleus, and a miRNA sequence having about 20 to 25 bases is cut out by Dicer. This is then incorporated into a complex of ribonucleic acid and Argonaute protein called RNA-induced silencing complex (RISC) to form an miRNA-RISC complex, which then binds to the 3'UTR of mRNA to suppress gene expression. Because the binding of miRNA to mRNA is incomplete, the number of target genes is not limited to one. Accordingly, it is an important feature that multiple genes can be targeted and regulated.

In addition, it has also been clarified that miRNA plays an important role in regulation of the gene expression in vivo, and abnormalities in the miRNA regulatory system are involved in cause and progression of many diseases. In particular, various miRNAs associated with onset and progression of cancer have been elucidated, and are attracting attention as leaders of nucleic acid drugs for treating cancer. Conventionally, various reports have been made on miRNAs that exhibit antitumor activity. Among them, miRNA34a has been reported to have a tumor growth inhibitory action (see Patent Document 1). Furthermore, among previously reported miRNAs, miRNA34a is considered to have the most effective anti-cancer effect on solid tumor. Accordingly, its feasibility as a nucleic acid drug is being considered. However, because cancer is a serious and life-threatening disease, there is a need for the development of miRNA that exerts a better antitumor effect.

On the other hand, cancer cells have a self-proliferation potency, and have the property of being capable of infiltration into a surrounding tissue and metastasis into a distant tissue. However, it has been found that not all cancer cells forming cancer tissue have such properties, but cancer cells developing or progressing cancer are cancer stem cells that rarely exist in cancer cells. Similar to normal stem cells, cancer stem cells exhibit an undifferentiated surface morphology, have a self-proliferation potency and differentiation potency, and have the property of producing any cancer cells constituting cancer tissue that are in various differentiation stages. In other words, cancer stem cells are considered to be the basis for generating a majority of cancer cells by differentiation, while maintaining the same cells as themselves by self-proliferation in cancer tissue.

However, conventionally, miRNAs that can suppress proliferation of cancer stem cells have not been reported. In addition, miRNA34a is considered to be the most effective anticancer effect on solid tumor among previously reported miRNAs, but even with miRNA34a, the proliferation inhibitory effect on cancer stem cells cannot be said to be sufficient at present.

PRIOR ART DOCUMENT

Patent Document

Patent Document 1: Japanese Patent Laid-open Publication No. 2008-239596

SUMMARY OF THE INVENTION

Problems to be Solved by the Invention

An object of the present invention is to provide a nucleic acid drug for cancer treatment, the drug being capable of suppressing proliferation of cancer stem cells and thus effectively treating cancer.

Means for Solving to Problem

The present inventors have carried out earnest studies to solve the above problems, and found that hsa-miR-136-5p, hsa-miR-3065-3p, hsa-miR-4727-5p, hsa-miR-378g, hsa-miR-181a-5p, hsa-miR-362-5p and hsa-miR-608 have a much better proliferation inhibitory effect on cancer stem cells and are thus useful as nucleic acid drugs for treating various cancers. More specifically, it has been found that each of the miRNAs is highly effective in suppressing proliferation of cancer stem cells and thus effective for treating cancer, and, for example, each of the miRNAs can effectively treat cancer in combination with an anticancer drug that exerts a proliferation inhibitory effect on non-cancer stem cells (cancer cells that are not cancer stem cells).

In addition, the present inventors have also found that each of the miRNAs is useful as a cancer therapeutic agent for each cancer described below.

hsa-miR-136-5p: esophageal cancer, gastric cancer, pancreatic cancer, liver cancer, large bowel cancer, prostate cancer, cervical cancer, kidney cancer, head and neck cancer, oral cancer and hematologic cancer hsa-miR-3065-3p: any cancer including solid cancer and hematologic cancer hsa-miR-4727-5p: any cancer including solid cancer and hematologic cancer hsa-miR-378g: esophageal cancer, pancreatic cancer, cervical cancer, thyroid cancer, kidney cancer, head and neck cancer and oral cancer hsa-miR-181a-5p: esophageal cancer, pancreatic cancer, thyroid cancer, kidney cancer, large bowel cancer, gastric cancer, liver cancer, breast cancer, prostate cancer, head and neck cancer and oral cancer hsa-miR-362-5p: esophageal cancer, pancreatic cancer, large bowel cancer, lung cancer, prostate cancer, cervical cancer, thyroid cancer, gastric cancer, liver cancer, head and neck cancer, oral cancer and hematologic cancer hsa-miR-608: esophageal cancer, gastric cancer, pancreatic cancer, liver cancer, breast cancer, lung cancer, prostate cancer, cervical cancer, thyroid cancer, kidney cancer, head and neck cancer, oral cancer and hematologic cancer The present invention has been completed by further conducting studies based on these findings. In other words, the present invention provides an invention of the aspects described below.

Item 1-1. An agent for inhibiting proliferation of cancer stem cell containing as an active ingredient at least one miRNA selected from the group consisting of hsa-miR-136-5p, hsa-miR-3065-3p, hsa-miR-4727-5p, hsa-miR-378g, hsa-miR-181a-5p, hsa-miR-362-5p and hsa-miR-608.

Item 1-2. The agent for inhibiting proliferation of cancer stem cell according to item 1-1, which is administered simultaneously with an anticancer drug, or before and/or after administration of an anticancer drug.

Item 1-3. The agent for inhibiting proliferation of cancer stem cell according to item 1-1 or 1-2, in which the miRNA is a mature miRNA, pri-miRNA or pre-miRNA.

Item 1-4. The agent for inhibiting proliferation of cancer stem cell according to any one of items 1-1 to 1-3, in which the miRNA is complexed to a carbonate apatite particle.

Item 1-5. Use of at least one miRNA selected from the group consisting of hsa-miR-136-5p, hsa-miR-3065-3p, hsa-miR-4727-5p, hsa-miR-378g, hsa-miR-181a-5p, hsa-miR-362-5p and hsa-miR-608 for the manufacture of an agent for inhibiting proliferation of cancer stem cell.

Item 1-6. The use according to item 1-5, in which the agent for inhibiting proliferation of cancer stem cell is administered simultaneously with an anticancer drug, or before and/or after administration of an anticancer drug.

Item 1-7. The use according to item 1-5 or 1-6, in which the miRNA is a mature miRNA, pri-miRNA or pre-miRNA.

Item 1-8. The use according to any one of items 1-5 to 1-7, in which the miRNA is complexed to a carbonate apatite particle.

Item 1-9. A method for treating cancer, including a step of administering to a cancer patient a therapeutically effective amount of at least one miRNA selected from the group consisting of hsa-miR-136-5p, hsa-miR-3065-3p, hsa-miR-4727-5p, hsa-miR-378g, hsa-miR-181a-5p, hsa-miR-362-5p and hsa-miR-608.

Item 1-10. The method for treating cancer according to item 1-9, in which the miRNA is administered simultaneously with an anticancer drug, or before and/or after administration of an anticancer drug.

Item 1-11. The method for treating cancer according to item 1-9 or 1-10, in which the miRNA is a mature miRNA, pri-miRNA or pre-miRNA.

Item 1-12. The method for treating cancer according to any one of items 1-9 to 1-11, in which the miRNA is complexed to a carbonate apatite particle.

Item 2-1. A therapeutic agent for treating esophageal cancer, gastric cancer, pancreatic cancer, liver cancer, large bowel cancer, prostate cancer, cervical cancer, kidney cancer, head and neck cancer, oral cancer, or hematologic cancer, the therapeutic agent containing hsa-miR-136-5p as an active ingredient.

Item 2-2. The therapeutic agent according to item 2-1, in which the hsa-miR-136-5p is a mature miRNA, pri-miRNA or pre-miRNA.

Item 2-3. The therapeutic agent according to item 2-1 or in which the hsa-miR-136-5p is complexed to a carbonate apatite particle.

Item 2-4. Use of hsa-miR-136-5p for the manufacture of a therapeutic agent for treating esophageal cancer, gastric cancer, pancreatic cancer, liver cancer, large bowel cancer, prostate cancer, cervical cancer, kidney cancer, head and neck cancer, oral cancer, or hematologic cancer.

Item 2-5. The use according to item 2-4, in which the hsa-miR-136-5p is a mature miRNA, pri-miRNA or pre-miRNA.

Item 2-6. The use according to item 2-4 or 2-5, in which the hsa-miR-136-5p is complexed to a carbonate apatite particle.

Item 2-7. A method for treating cancer, including a step of administering a therapeutically effective amount of hsa-miR-136-5p to a cancer patient with esophageal cancer, gastric cancer, pancreatic cancer, liver cancer, large bowel cancer, prostate cancer, cervical cancer, kidney cancer, head and neck cancer, oral cancer or hematologic cancer.

Item 2-8. The method for treating cancer according to item 2-7, in which the hsa-miR-136-5p is a mature miRNA, pri-miRNA or pre-miRNA.

Item 2-9. The method for treating cancer according to item 2-7 or 2-8, in which the hsa-miR-136-5p is complexed to a carbonate apatite particle.

Item 3-1. A therapeutic agent for cancer containing hsa-miR-3065-3p and/or hsa-miR-4727-5p as an active ingredient.

Item 3-2. The therapeutic agent according to item 3-1, in which the hsa-miR-3065-3p and/or hsa-miR-4727-5p is a mature miRNA, pri-miRNA or pre-miRNA.

Item 3-3. The therapeutic agent according to item 3-1 or 3-2, in which the hsa-miR-3065-3p and/or hsa-miR-4727-5p is complexed to a carbonate apatite particle.

Item 3-4. Use of hsa-miR-3065-3p and/or hsa-miR-4727-5p for producing a therapeutic agent for cancer.

Item 3-5. The use according to item 3-4, in which the hsa-miR-3065-3p and/or hsa-miR-4727-5p is a mature miRNA, pri-miRNA or pre-miRNA.

Item 3-6. The use according to item 3-4 or 3-5, in which the hsa-miR-3065-3p and/or hsa-miR-4727-5p is complexed to a carbonate apatite particle.

Item 3-7. A method for treating cancer, including a step of administering to a cancer patient a therapeutically effective amount of hsa-miR-3065-3p and/or hsa-miR-4727-5p.

Item 3-8. The method for treating cancer according to item 3-7, in which the hsa-miR-3065-3p and/or hsa-miR-4727-5p is a mature miRNA, pri-miRNA or pre-miRNA.

Item 3-9. The method for treating cancer according to item 3-7 or 3-8, in which the hsa-miR-3065-3p and/or hsa-miR-4727-5p is complexed to a carbonate apatite particle.

Item 4-1. A therapeutic agent for treating esophageal cancer, pancreatic cancer, cervical cancer, thyroid cancer, kidney cancer, head and neck cancer, or oral cancer, the therapeutic agent containing hsa-miR-378g as an active ingredient.

Item 4-2. The therapeutic agent according to item 4-1, in which the hsa-miR-378g is a mature miRNA, pri-miRNA or pre-miRNA.

Item 4-3. The therapeutic agent according to item 4-1 or 4-2, in which the hsa-miR-378g is complexed to a carbonate apatite particle.

Item 4-4. Use of hsa-miR-378g for producing a therapeutic agent for esophageal cancer, pancreatic cancer, cervical cancer, thyroid cancer, kidney cancer, head and neck cancer, or oral cancer.

Item 4-5. The use according to item 4-4, in which the hsa-miR-378g is a mature miRNA, pri-miRNA or pre-miRNA.

Item 4-6. The use according to item 4-4 or 4-5, in which the hsa-miR-378g is complexed to a carbonate apatite particle.

Item 4-7. A method for treating cancer, including a step of administering a therapeutically effective amount of hsa-miR-378g to a patient with esophageal cancer, pancreatic cancer, cervical cancer, thyroid cancer, kidney cancer, head and neck cancer, or oral cancer.

Item 4-8. The method for treating cancer according to item 4-7, in which the hsa-miR-378g is a mature miRNA, pri-miRNA or pre-miRNA.

Item 4-9. The method for treating cancer according to item 4-7 or 4-8, in which the hsa-miR-378g is complexed to a carbonate apatite particle.

Item 5-1. A therapeutic agent for treating esophageal cancer, pancreatic cancer, thyroid cancer, kidney cancer, large bowel cancer, gastric cancer, liver cancer, breast cancer, prostate cancer, head and neck cancer, or oral cancer, the therapeutic agent containing hsa-miR-181a-5p as an active ingredient.

Item 5-2. The therapeutic agent according to item 5-1, in which the hsa-miR-181a-5p is a mature miRNA, pri-miRNA or pre-miRNA.

Item 5-3. The therapeutic agent according to item 5-1 or 5-2, in which the hsa-miR-181a-5p is complexed to a carbonate apatite particle.

Item 5-4. Use of hsa-miR-181a-5p for the manufacture of a therapeutic agent for treating esophageal cancer, pancreatic cancer, thyroid cancer, kidney cancer, large bowel cancer, gastric cancer, liver cancer, breast cancer, prostate cancer, head and neck cancer, or oral cancer.

Item 5-5. The use according to item 5-4, in which the hsa-miR-181a-5p is a mature miRNA, pri-miRNA or pre-miRNA.

Item 5-6. The use according to item 5-4 or 5-5, in which the hsa-miR-181a-5p is complexed to a carbonate apatite particle.

Item 5-7. A method for treating cancer, including a step of administering a therapeutically effective amount of hsa-miR-181a-5p to a patient with esophageal cancer, pancreatic cancer, thyroid cancer, kidney cancer, large bowel cancer, gastric cancer, liver cancer, breast cancer, prostate cancer, head and neck cancer, or oral cancer.

Item 5-8. The method for treating cancer according to item 5-7, in which the hsa-miR-181a-5p is a mature miRNA, pri-miRNA or pre-miRNA.

Item 5-9. The method for treating cancer according to item 5-7 or 5-8, in which the hsa-miR-181a-5p is complexed to a carbonate apatite particle.

Item 6-1. A therapeutic agent for treating esophageal cancer, pancreatic cancer, large bowel cancer, lung cancer, prostate cancer, cervical cancer, thyroid cancer, gastric cancer, liver cancer, head and neck cancer, oral cancer, or hematologic cancer, the therapeutic agent containing hsa-miR-362-5p as an active ingredient.

Item 6-2. The therapeutic agent according to item 6-1, in which the hsa-miR-362-5p is a mature miRNA, pri-miRNA or pre-miRNA.

Item 6-3. The therapeutic agent according to item 6-1 or 6-2, in which the hsa-miR-362-5p is complexed to a carbonate apatite particle.

Item 6-4. Use of hsa-miR-362-5p for the manufacture of a therapeutic agent for treating esophageal cancer, pancreatic cancer, large bowel cancer, lung cancer, prostate cancer, cervical cancer, thyroid cancer, gastric cancer, liver cancer, head and neck cancer, oral cancer, or hematologic cancer.

Item 6-5. The use according to item 6-4, in which the hsa-miR-362-5p is a mature miRNA, pri-miRNA or pre-miRNA.

Item 6-6. The use according to item 6-4 or 6-5, in which the hsa-miR-362-5p is complexed to a carbonate apatite particle.

Item 6-7. A method for treating cancer, including a step of administering a therapeutically effective amount of hsa-miR-362-5p to a patient with esophageal cancer, pancreatic cancer, large bowel cancer, lung cancer, prostate cancer, cervical cancer, thyroid cancer, gastric cancer, liver cancer, head and neck cancer, oral cancer, or hematologic cancer.

Item 6-8. The method for treating cancer according to item 6-7, in which the hsa-miR-362-5p is a mature miRNA, pri-miRNA or pre-miRNA.

Item 6-9. The method for treating cancer according to item 6-7 or 6-8, in which the hsa-miR-362-5p is complexed to a carbonate apatite particle.

Item 7-1. A therapeutic agent for treating esophageal cancer, gastric cancer, pancreatic cancer, liver cancer, breast cancer, lung cancer, hematologic cancer, prostate cancer, cervical cancer, thyroid cancer, kidney cancer, head and neck cancer, oral cancer, or hematologic cancer, the therapeutic agent containing hsa-miR-608 as an active ingredient.

Item 7-2. The therapeutic agent according to item 7-1, in which the hsa-miR-608 is a mature miRNA, pri-miRNA or pre-miRNA.

Item 7-7. The therapeutic agent according to item 7-1 or 7-2, in which the hsa-miR-608 is complexed to a carbonate apatite particle.

Item 7-4. Use of hsa-miR-608 for the manufacture of a therapeutic agent for treating esophageal cancer, gastric cancer, pancreatic cancer, liver cancer, breast cancer, lung cancer, hematologic cancer, prostate cancer, cervical cancer, thyroid cancer, kidney cancer, head and neck cancer, oral cancer, or hematologic cancer.

Item 7-5. The use according to item 7-4, in which the hsa-miR-608 is a mature miRNA, pri-miRNA or pre-miRNA.

Item 7-6. The use according to item 7-4 or 7-5, in which the hsa-miR-608 is complexed to a carbonate apatite particle.

Item 7-7. A method for treating cancer, including a step of administering a therapeutically effective amount of hsa-miR-608 to a patient with esophageal cancer, gastric cancer, pancreatic cancer, liver cancer, breast cancer, lung cancer, hematologic cancer, prostate cancer, cervical cancer, thyroid cancer, kidney cancer, head and neck cancer, oral cancer or hematologic cancer.

Item 7-8. The method for treating cancer according to item 7-7, in which the hsa-miR-608 is a mature miRNA, pri-miRNA or pre-miRNA.

Item 7-9. The method for treating cancer according to item 7-7 or 7-8, in which the hsa-miR-608 is complexed to a carbonate apatite particle.

Advantages of the Invention

The agent for inhibiting proliferation of cancer stem cell of the present invention can effectively lead to proliferation suppression or death of cancer stem cells, and thus has extremely high clinical utility as a nucleic acid drug for treating cancer. In particular, the agent for inhibiting proliferation of cancer stem cell of the present invention can effectively exert a proliferation inhibitory effect on both cancer stem cells and non-cancer stem cells using an anticancer drug that exerts a proliferation inhibitory effect on non-cancer stem cells (cancer cells that are not cancer stem cells) in combination, thereby drastically improving the therapeutic effect on cancer.

Furthermore, the agent for inhibiting proliferation of cancer stem cell of the present invention can exert an antitumor effect which is much better than already reported antitumor effects of miRNAs, so that it is effective as a therapeutic agent for various cancers even when used alone.

BRIEF DESCRIPTION OF THE DRAWINGS

In FIG. 5a, the result of the tumor volume measured over time is shown, in FIG. 5b, the result of observation of the tumor excised on the 24th day is shown, and in FIG. 5c, the result of the measured weight of the tumor excised on the 24th day is shown.

In FIG. 6a, the result of the tumor volume measured over time is shown, and in FIG. 6b, the result of observation of the tumor excised on the 24th day is shown.

EMBODIMENTS OF THE INVENTION

Figure 1:
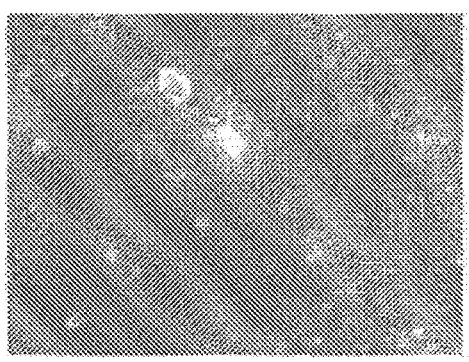
FIG. 1a shows the result of observation with a fluorescence microscope of a cancer stem cell line (about 0.06%) established by introducing an ornithine decarboxylase (ODC)-degron system into a pancreatic cancer cell line Panc-1.
FIG. 1b shows the result of observation of a cancer stem cell line before and after enrichment of the cancer stem cell line. The upper views in FIG. 1b are the result of observation of a cell population before enrichment, and the lower views are the result of observation of a cell population after enrichment.
Figure 1:
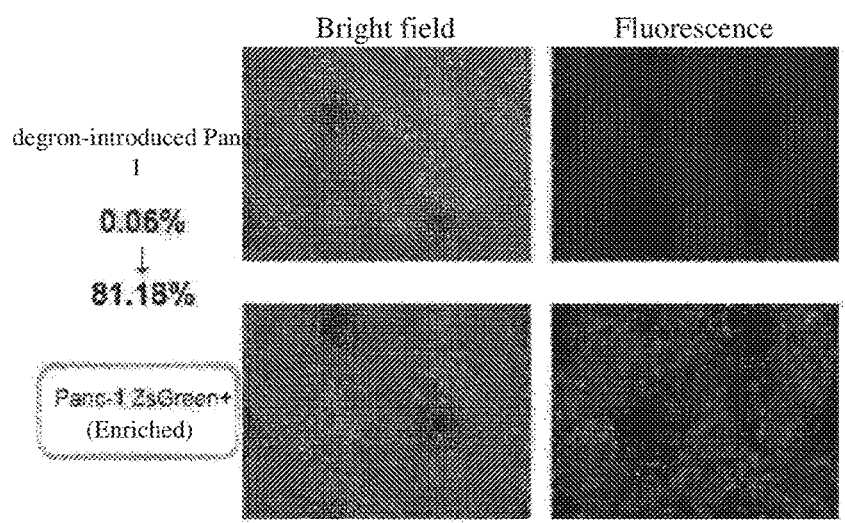

1. Proliferation Inhibitor of Cancer Stem Cell

One aspect of the present invention is an agent for inhibiting proliferation of cancer stem cell containing as an active ingredient at least one miRNA selected from the group consisting of hsa-miR-136-5p, hsa-miR-3065-3p, hsa-miR-4727-5p, hsa-miR-378g, hsa-miR-181a-5p, hsa-miR-362-5p and hsa-miR-608. Hereinafter, a description is made of the agent for inhibiting proliferation of cancer stem cell of the present invention.

(Active Ingredient)

The hsa-miR-136-5p is human-derived miR-136-5p, and its base sequence is the base sequence set forth in SEQ ID NO: 1 when it is a mature miRNA (mature-miRNA).

The hsa-miR-3065-3p is human-derived miR-3065-3p, and its base sequence is the base sequence set forth in SEQ ID NO: 2 when it is a mature miRNA (mature-miRNA).

The hsa-miR-4727-5p is human-derived miR-4727-5p, and its base sequence is the base sequence set forth in SEQ ID NO: 3 when it is a mature miRNA (mature-miRNA).

The hsa-miR-378g is human-derived miR-378g, and its base sequence is the base sequence set forth in SEQ ID NO: 4 when it is a mature miRNA (mature-miRNA).

The hsa-miR-181a-5p is human-derived miR-181a-5p, and its base sequence is the base sequence set forth in SEQ ID NO: 5 when it is a mature miRNA (mature-miRNA).

The hsa-miR-362 is human-derived miR-362-5p, and its base sequence is the base sequence set forth in SEQ ID NO: 6 when it is a mature miRNA (mature-miRNA).

The hsa-miR-608 is human-derived miR-608, and its base sequence is the base sequence set forth in SEQ ID NO: 7 when it is a mature miRNA (mature-miRNA).

The agent for inhibiting proliferation of cancer stem cell of the present invention may use as an active ingredient one type of miRNA selected from the hsa-miR-136-5p, hsa-miR-3065-3p, hsa-miR-4727-5p, hsa-miR-378g, hsa-miR-181a-5p, hsa-miR-362-5p and hsa-miR-608 alone, or two or more types thereof in combination.

In addition, each miRNA used as an active ingredient may be a mature miRNA, a hairpin-type precursor miRNA (pri-miRNA), or a pre-miRNA in which a part of the pri-miRNA is cleaved. The pri-miRNA or pre-miRNA is processed in cells to become the mature miRNA. In addition, each of the miRNAs may form a double-stranded precursor with an RNA having a complementary base sequence. The double-stranded precursor gets loose in cancer cells to release the mature miRNA. The base sequence of the hairpin-type precursor miRNA or the pre-miRNA may be set to generate a polynucleotide composed of a desired base sequence as the mature miRNA, and such a base sequence can be appropriately set by a person skilled in the art.

Each miRNA used as an active ingredient may be subjected to various modifications that are generally applied to nucleic acids, as necessary, to impart degradation resistance to enzyme or the like. Examples of such modifications include modification of a carbohydrate chain moiety such as 2'-O methylation; modification of a base moiety; modification of a phosphate moiety such as amination, lower alkyl amination, acetylation and the like.

(Use)

The agent for inhibiting proliferation of cancer stein cell of the present invention can effectively suppress proliferation of cancer stem cells, and thus can be used for treatment of various cancers.

The cancer type to which the agent for inhibiting proliferation of cancer stem cell of the present invention is applied is not particularly limited, but examples thereof include solid cancer such as esophageal cancer, large bowel cancer, colon cancer, gastric cancer, rectal cancer, liver cancer, pancreatic cancer, lung cancer, breast cancer, bladder cancer, prostate cancer, cervical cancer, kidney cancer, brain tumor, head and neck cancer, cholangiocarcinoma, gallbladder cancer and oral cancer; and hematologic cancer such as leukemia and malignant lymphoma. Among these cancer types, preferably included is solid cancer, more preferably included are pancreatic cancer, gastric cancer, esophageal cancer and large bowel cancer.

In addition, when used to cancer for which no therapeutic effect has been observed in other chemotherapy, the agent for inhibiting proliferation of cancer stem cell of the present invention can also effectively treat the cancer by suppressing proliferation of cancer stem cells.

In addition, by suppressing proliferation of not only cancer stem cells but also non-cancer stem cells (cancer cells that are not cancer stem cells), the therapeutic effect on cancer can be drastically improved. Accordingly, a preferred aspect of the use of the agent for inhibiting proliferation of cancer stem cell of the present invention includes co-administration with another anticancer drug. The type of the anticancer drug used in combination with the agent for inhibiting proliferation of cancer stem cell of the present invention is not particularly limited, but examples thereof include an antimetabolite, platinum preparation, alkylating agent, microtubule agonist, anticancer antibiotic and topoisomerase inhibitor. Specific examples of the antimetabolite include 5-fluorouracil, methotrexate, doxilluridine. Tegafur, cytarabine and gemcitahine. Specific examples of the platinum preparation include cisplatin, oxaliplatin, carboplatin and nedaplatin. Specific examples of the alkylating agent include cyclophosphamide, ifosfamide, thiotepa, carboquone and nimustine hydrochloride. Specific examples of the microtubule agonist include docetaxel, paclitaxel, vincristine, vindesine and vinorelbine. Specific examples of the anticancer antibiotic include doxorubicin hydrochloride, mitomycin, amrubicin hydrochloride, pirarubicin hydrochloride, epirubicin hydrochloride, aclarubicin hydrochloride, mitoxantrone hydrochloride, bleomycin hydrochloride and peplomycin sulfate. Specific examples of the topoisomerase inhibitor include irinotecan and nogitecan hydrochloride.

When the agent for inhibiting proliferation of cancer stem cell of the present invention is administered in combination with the other anticancer drug, the agent for inhibiting proliferation of cancer stem cell of the present invention and the other anticancer drug may be simultaneously administered, or the agent for inhibiting proliferation of cancer stem cell of the present invention and the other anticancer drug may be separately administered in any order. When the agent for inhibiting proliferation of cancer stem cell of the present invention and the other anticancer drug are separately administered in any order, for example, within about 3 hours or about 1 to 14 days (particularly, about 3 to 14 days) after administration of the agent for inhibiting proliferation of cancer stem cell of the present invention, the anticancer drug may be administered, or within about 3 hours or about 1 to 14 days (particularly after about 3 to 14 days) after administration of the anticancer drug, the agent for inhibiting proliferation of cancer stem cell of the present invention may be administered. Although the number of administration of the agent for inhibiting proliferation of cancer stem cell of the present invention and the other anticancer drug may be appropriately set depending on the condition of the patient, for example, they may be each administered once, or either one or both of the agent for inhibiting proliferation of cancer stem cell of the present invention and another anticancer drug may be administered twice or more.

(Administration Method)

The administration method for the agent for inhibiting proliferation of cancer stem cell of the present invention is not particularly limited as long as the miRNA can be delivered to the tissue or cells of the cancer in vivo, but examples of the method include intravascular (intraarterial or intravenous) injection, continuous infusion, subcutaneous administration, topical administration, intramuscular administration and intraperitoneal administration. Among them, preferably included is intraarterial or intravenous administration.

The dose of the agent for inhibiting proliferation of cancer stem cell of the present invention is appropriately determined depending on the type of cancer stem cells to be applied, the sex, age or symptom of the patient etc., so that it cannot be generally determined, but for example, in terms of the amount of mature miRNA of the miRNA, about 1 to 100 mg/m$^2$ (body surface area) per day is included.

The agent for inhibiting proliferation of cancer stem cell of the present invention exerts a proliferation inhibitory effect on cancer stem cells by the functional expression of the miRNA when delivered into cancer stem cells. Accordingly, the agent for inhibiting proliferation of cancer stem cell of the present invention is desirable to be formulated with an miRNA transfer agent in order to facilitate delivery of the miRNA into cancer cells. Such an miRNA transfer agent is not particularly limited, but may be any of carbonate apatite particles, Lipofectamine, Oligofectamine, RNAiFect and the like. Among these miRNA transfer agents, carbonate apatite particles can provide efficient accumulation and migration into cancer cells in vivo. Accordingly, a preferred aspect of the agent for inhibiting proliferation of cancer stem cell of the present ion includes those in which the miRNA is present in a mixed state with a carbonate apatite particle, or the miRNA is present in a complexed state with a carbonate apatite particle to form a composite particle. A description of the carbonate apatite particle used as a transfer agent for the miRNA is made in the column of "8. Suitable miRNA transfer agent (carbonate apatite particle)."

2. Cancer Therapeutic Agent Using hsa-miR-136-5p

One aspect of the present invention is a therapeutic agent for esophageal cancer, gastric cancer, pancreatic cancer, liver cancer, large bowel cancer, prostate cancer, cervical cancer, kidney cancer, head and neck cancer, oral cancer, or hematologic cancer (leukemia, malignant lymphoma etc.), the therapeutic agent containing hsa-miR-136-5p as an active ingredient (hereinafter, sometimes referred to as "cancer therapeutic agent A"). Hereinafter, a description is made of the cancer therapeutic agent A.

(Active Ingredient)

The hsa-miR-136-5p used as an active ingredient in the cancer therapeutic agent A is human-derived miR-136-5p, the base sequence of which is as described above.

The hsa-miR-136-5p may be a mature miRNA, a hairpin-type precursor miRNA (pri-miRNA), or a pre-miRNA in which a part of the pri-miRNA is cleaved. The pri-miRNA or pre-miRNA is processed in cells to become the mature miRNA. In addition, the miRNA136-5p may form a double-stranded precursor with an RNA having a complementary base sequence. The double-stranded precursor gets loose in cancer cells to release the mature miRNA. The base sequence of the hairpin-type precursor hsa-miR-136-5p or pre-hsa-miR-136-5p may be set to generate a polynucleotide composed of the base sequence set forth in SEQ ID NO: 1 as the mature miRNA, and such a base sequence can be appropriately set by a person skilled in the art.

The hsa-miR-136-5p may be subjected to various modifications that are generally applied to nucleic acids, as necessary, to impart degradation resistance to enzyme or the like. Examples of such modifications include modification of a carbohydrate chain moiety such as 2'-O methylation; modification of a base moiety; modification of a phosphate moiety such as amination, lower alkyl amination, acetylation and the like.

(Application)

Cancer types to which the cancer therapeutic agent A is applied are esophageal cancer, gastric cancer, pancreatic cancer, liver cancer, large bowel cancer, prostate cancer, cervical cancer, kidney cancer, head and neck cancer, oral cancer, or hematologic cancer (leukemia, malignant lymphoma etc.). The cancer therapeutic agent A can suppress proliferation of cancer stem cells of these cancer tissues, and thus can effectively treat these cancers.

Among the cancers to be treated e cancer therapeutic agent A, preferably included are gastric cancer, pancreatic cancer, esophageal cancer and large bowel cancer.

(Administration Method)

The administration method for the cancer therapeutic agent A is not particularly limited as long as the cancer therapeutic agent A can be delivered to the tissue or cells of the cancer in vivo, but examples of the method include intravascular (intraarterial or intravenous) injection, continuous infusion, subcutaneous administration, topical administration, intramuscular administration and intraperitoneal administration. Among them, preferably included is intraarterial or intravenous administration.

The dose of the cancer therapeutic agent A is appropriately determined depending on the cancer type, the sex, age or symptom of the patient etc., so that it cannot be generally determined, but for example, in terms of the amount of mature miRNA of the hsa-miR-136-5p, about 1 to 100 mg/m$^2$ (body surface area) per day is included.

The cancer therapeutic agent A exerts a cancer therapeutic effect by the functional expression of the hsa-miR-136-5p when delivered into cells (in particular, into cancer stem cells) of the cancer. Accordingly, the cancer therapeutic agent A is desirable to be formulated with an miRNA transfer agent in order to facilitate delivery of the hsa-miR-136-5p into cancer cells. Such an miRNA transfer agent is not particularly limited, but may be any of carbonate apatite particles, Lipofectamine, Oligofectamine, RNAiFect and the like. Among these miRNA transfer agents, carbonate apatite particles can provide efficient accumulation and migration into cancer cells in vivo. Accordingly, a preferred aspect of the cancer therapeutic agent A includes those in which the hsa-miR-136-5p is present in a mixed state with a carbonate apatite particle, or the hsa-miR-136-5p is present in a complexed state with a carbonate apatite particle to form a composite particle. A description of the carbonate apatite particle used as a transfer agent for the hsa-miR-136-5p is made in the column of "8. Suitable miRNA transfer agent (carbonate apatite particle)."

3. Cancer Therapeutic Agent Using hsa-miR-3065-3p and/or hsa-miR-4727-5p

One aspect of the present invention is a therapeutic agent for cancer, the therapeutic agent containing hsa-miR-3065-3p and/or hsa-miR-4727-5p as an active ingredient (hereinafter, sometimes referred to as "cancer therapeutic agent B"). Hereinafter, a description is made of the cancer therapeutic agent B.

(Active Ingredient)

The hsa-miR-3065-3p used as an active ingredient in the cancer therapeutic agent B is human-derived miR-3065-3p, the base sequence of which is as described above. In addition, the hsa-miR-4727-5p used as an active ingredient in the cancer therapeutic agent B is human-derived miR-4727-5p, the base sequence of which is as described above. In the cancer therapeutic agent B, either one of the hsa-miR-3065-3p or hsa-miR-4727-5p may be used alone as an active ingredient, or these may be used in combination.

The miRNA used in the cancer therapeutic agent B may be a mature miRNA, a hairpin-type precursor miRNA (pri-miRNA), or a pre-miRNA in which a part of the pri-miRNA is cleaved. The pri-miRNA or pre-miRNA is processed in cells to become the mature miRNA. In addition, the miRNA used in the cancer therapeutic agent B may form a double-stranded precursor with an RNA having a complementary base sequence. The double-stranded precursor gets loose in cancer cells to release the mature miRNA. The base sequence of the hairpin-type precursor miRNA or the pre-miRNA may be set to generate a desired mature miRNA, and such a base sequence can be appropriately set by a person skilled in the art.

The miRNA used in the cancer therapeutic agent B may be subjected to various modifications that are generally applied to nucleic acids, as necessary, to impart degradation resistance to enzyme or the like. Examples of such modifications include modification of a carbohydrate chain moiety such as 2'-O methylation; modification of a base moiety; modification of a phosphate moiety such as amination, lower alkyl amination, acetylation and the like.

(Application)

The cancer type to be treated with the cancer therapeutic agent B is not particularly limited as long as it is a cancer to which chemotherapy is to be applied, but examples thereof include solid cancer such as esophageal cancer, large bowel cancer, colon cancer, gastric cancer, rectal cancer, liver cancer, pancreatic cancer, lung cancer, breast cancer, bladder cancer, prostate cancer, cervical cancer, kidney cancer, brain tumor, head and neck cancer, cholangiocarcinoma, gallbladder cancer, oral cancer, skin cancer, endometrial cancer and thyroid cancer and hematologic cancer such as leukemia and malignant lymphoma. The cancer therapeutic agent B can suppress proliferation of cancer stem cells of the cancer tissues, and thus can effectively treat these cancers.

Among the cancers to be treated with the cancer therapeutic agent B, preferably included is solid cancer, more preferably included are gastric cancer, pancreatic cancer, large bowel cancer and esophageal cancer.

(Administration Method)

The administration method for the cancer therapeutic agent B is not particularly limited as long as the hsa-miR-3065-3p and/or hsa-miR-4727-5p can be delivered to the tissue or cells of the cancer in vivo, but examples of the method include intravascular (intraarterial or intravenous) injection, continuous infusion, subcutaneous administration, topical administration, intramuscular administration and intraperitoneal administration. Among them, preferably included is intraarterial or intravenous administration.

The dose of the cancer therapeutic agent B is appropriately determined depending on the cancer type, the sex, age or symptom of the patient etc., so that it cannot be generally determined, but for example, in terms of the amount of mature miRNA of the miRNA, hsa-miR-3065-3p and/or hsa-miR-4727-5p, about 1 to 100 mg/m² (body surface area) per day is included.

The cancer therapeutic agent B exerts a cancer therapeutic effect by the functional expression of the hsa-miR-3065-3p and/or hsa-miR-4727-5p when delivered into cells (in particular, into cancer stem cells) of the cancer. Accordingly, the cancer therapeutic agent B is desirable to be formulated with an miRNA transfer agent in order to facilitate delivery of the hsa-miR-3065-3p and/or hsa-miR-4727-5p into cancer cells. Such an miRNA transfer agent is not particularly limited, but may be any of carbonate apatite particles, Lipofectamine, Oligofectamine, RNAiFect and the like. Among these miRNA transfer agents, carbonate apatite particles can provide efficient accumulation and migration into cancer cells in vivo. Accordingly, a preferred aspect of the cancer therapeutic agent B includes those in which the hsa-miR-3065-3p and/or hsa-miR-4727-5p is present in a mixed state with a carbonate apatite particle, or the hsa-miR-3065-3p and/or hsa-miR-4727-5p is present in a complexed state with a carbonate apatite particle to form a composite particle. A description of the carbonate apatite particle used as a transfer agent for the hsa-miR-3065-3p and/or hsa-miR-4727-5p is made in the column of "8. Suitable miRNA transfer agent (carbonate apatite particle)."

4. Cancer Therapeutic Agent Using hsa-miR-378g

One aspect of the present invention is a therapeutic agent for esophageal cancer, pancreatic cancer, cervical cancer, thyroid cancer, kidney cancer, head and neck cancer or oral cancer, the therapeutic agent containing hsa-miR-378g as an active ingredient (hereinafter, sometimes referred to as "cancer therapeutic agent C"). Hereinafter, a description is made of the cancer therapeutic agent C.

(Active Ingredient)

The hsa-miR-378g used as an active ingredient in the cancer therapeutic agent C is human-derived miR-378g, the base sequence of which is as described above.

The hsa-miR-378g may be a mature miRNA, a hairpin-type precursor miRNA (pri-miRNA), or a pre-miRNA in which a part of the pri-miRNA is cleaved. The pri-miRNA or pre-miRNA is processed in cells to become the mature miRNA. In addition, the miRNA378g may form a double-stranded precursor with an RNA having a complementary base sequence. The double-stranded precursor gets loose in cancer cells to release the mature miRNA. The base sequence of the hairpin-type precursor hsa-miR-378g or pre-hsa-miR-378g may be set to generate a polynucleotide composed of the base sequence set forth in SEQ ID NO: 4 as the mature miRNA, and such a base sequence can be appropriately set by a person skilled in the art.

The hsa-miR-378 may be subjected to various modifications that are generally applied to nucleic acids, as necessary, to impart degradation resistance to enzyme or the like. Examples of such modifications include modification of a carbohydrate chain moiety such as 2'-O methylation; modification of a base moiety; modification of a phosphate moiety such as amination, lower alkyl amination, acetylation and the like.

(Application)

The cancer type to which the cancer therapeutic agent C is applied is esophageal cancer, pancreatic cancer, cervical cancer, thyroid cancer, kidney cancer, head and neck cancer or oral cancer. The cancer therapeutic agent C can suppress proliferation of cancer stem cells of these cancer tissues, and thus can effectively treat these cancers.

Among the cancers to be treated with the cancer therapeutic agent C, preferably included are pancreatic cancer and esophageal cancer.

(Administration Method)

The administration method for the cancer therapeutic agent C is not particularly limited as long as the cancer therapeutic agent C can be delivered to the tissue or cells of the cancer in vivo, but examples of the method include intravascular (intraarterial or intravenous) injection, continuous infusion, subcutaneous administration, topical administration, intramuscular administration and intraperitoneal administration. Among them, preferably included is intraarterial or intravenous administration.

The dose of the cancer therapeutic agent C is appropriately determined depending on the cancer type, the sex, age or symptom of the patient etc., so that it cannot be generally determined, but for example, in terms of the amount of mature miRNA of the hsa-miR-378g, about 1 to 100 mg/m² (body surface area) per day is included.

The cancer therapeutic agent C exerts a cancer therapeutic effect by the functional expression of the hsa-miR-378g when delivered into cells (in particular, into cancer stem cells) of the cancer. Accordingly, the cancer therapeutic agent C is desirable to be formulated with an miRNA transfer agent in order to facilitate delivery of the hsa-miR-378g into cancer cells. Such an miRNA transfer agent is not particularly limited, but may be any of carbonate apatite particles, Lipofectamine, Oligofectamine, RNAiFect and the like. Among these miRNA transfer agents, carbonate apatite particles can provide efficient accumulation and migration into cancer cells in vivo. Accordingly, a preferred aspect of the cancer therapeutic agent C includes those in which the hsa-miR-378g is present in a mixed state with a carbonate apatite particle, or the hsa-miR-378g is present in a complexed state with a carbonate apatite particle to form a composite particle. A description of the carbonate apatite particle used as a transfer agent for the hsa-miR-378g is made in the column of "8. Suitable miRNA transfer agent (carbonate apatite particle)."

5. Cancer Therapeutic Agent Using hsa-miR-181a-5p

One aspect of the present invention is a therapeutic agent for esophageal cancer, pancreatic cancer, thyroid cancer, kidney cancer, large bowel cancer, gastric cancer, liver cancer, breast cancer, prostate cancer, head and neck cancer or oral cancer, the therapeutic agent containing hsa-miR- 181a-5p as an active ingredient (hereinafter, sometimes referred to as "cancer therapeutic agent D"). Hereinafter, a description is made of the cancer therapeutic agent D.

(Active Ingredient)

The hsa-miR-181a-5p used as an active ingredient in the cancer therapeutic agent D is human-derived miR-181a-5p, the base sequence of which is as described above.

The hsa-miR-181a-5p may be a mature miRNA, a hairpin-type precursor miRNA (pri-miRNA), or a pre-miRNA in which a part of the pri-miRNA is cleaved. The pri-miRNA or pre-miRNA is processed in cells to become the mature miRNA. In addition, the hsa-miR-181a-5p may form a double-stranded precursor with an RNA having a complementary base sequence. The double-stranded precursor gets loose in cancer cells to release the mature miRNA. The base sequence of the hairpin-type precursor hsa-miR-181a-5p or pre-hsa-miR-181a-5p may be set to generate a polynucleotide composed of the base sequence set forth in SEQ ID NO: 5 as the mature miRNA, and such a base sequence can be appropriately set by a person skilled in the art.

The hsa-miR-181a-5p may be subjected to various modifications that are generally applied to nucleic acids, as necessary, to impart degradation resistance to enzyme or the like. Examples of such modifications include modification of a carbohydrate chain moiety such as 2'-O methylation; modification of a base moiety; modification of a phosphate moiety such as amination, lower alkyl amination, acetylation and the like.

(Application)

The cancer type to which the cancer therapeutic agent D is applied is esophageal cancer, pancreatic cancer, thyroid cancer, kidney cancer, large bowel cancer, gastric cancer, liver cancer, breast cancer, prostate cancer, head and neck cancer or oral cancer. The cancer therapeutic agent D can suppress proliferation of cancer stem cells of these cancer tissues, and thus can effectively treat these cancers.

Among the cancers to be treated with the cancer therapeutic agent D, preferably included are pancreatic cancer, gastric cancer, large bowel cancer and esophageal cancer.

(Administration Method)

The administration method for the cancer therapeutic agent D is not particularly limited as long as the cancer therapeutic agent D can be delivered to the tissue or cells of the cancer in vivo, but examples of the method include intravascular (intraarterial or intravenous) injection, continuous infusion, subcutaneous administration, topical administration, intramuscular administration and intraperitoneal administration. Among them, preferably included is intraarterial or intravenous administration.

The dose of the cancer therapeutic agent D is appropriately determined depending on the cancer type, the sex, age or symptom of the patient etc., so that it cannot be generally determined, but for example, in terms of the amount of mature miRNA of the hsa-miR-181a-5p, about 1 to 100 mg/m$^2$ (body surface area) per day is included.

The cancer therapeutic agent D exerts a cancer therapeutic effect by the functional expression of the hsa-miR-181a-5p when delivered into cells (in particular, into cancer stem cells) of the cancer. Accordingly, the cancer therapeutic agent D is desirable to be formulated with an miRNA transfer agent in order to facilitate delivery of the hsa-miR-181a-5p into cancer cells. Such an miRNA transfer agent is not particularly limited, but may be any of carbonate apatite particles, Lipofectamine, Oligofectamine, RNAiFect and the like. Among these miRNA transfer agents, carbonate apatite particles can provide efficient accumulation and migration into cancer cells in vivo. Accordingly, a preferred aspect of the cancer therapeutic agent D includes those in which the hsa-miR-181a-5p is present in a mixed state with a carbonate apatite particle, or the hsa-miR-181a-5p is present in a complexed state with a carbonate apatite particle to form a composite particle. A description of the carbonate apatite particle used as a transfer agent for the hsa-miR-181a-5p is made in the column of "8. Suitable miRNA transfer agent (carbonate apatite particle)."

6. Cancer Therapeutic Agent Using hsa-miR-362-5p

One aspect of the present invention is a therapeutic agent for esophageal cancer, pancreatic cancer, large bowel cancer, lung cancer, prostate cancer, cervical cancer, thyroid cancer, gastric cancer, liver cancer, head and neck cancer, oral cancer, or hematologic cancer (leukemia, malignant lymphoma etc.), the therapeutic agent containing hsa-miR-362-5p as an active ingredient (hereinafter, sometimes referred to as "cancer therapeutic agent E"). Hereinafter, a description is made of the cancer therapeutic agent E.

(Active Ingredient)

The hsa-miR-362-5p used as an active ingredient in the cancer therapeutic agent E is human-derived miR-362-5p, the base sequence of which is as described above.

The hsa-miR-362-5p may be a mature miRNA, a hairpin-type precursor miRNA (pri-miRNA), or a pre-miRNA in which a part of the pri-miRNA is cleaved. The pri-miRNA or pre-miRNA is processed in cells to become the mature miRNA. In addition, the hsa-miR-362-5p may form a double-stranded precursor with an RNA having a complementary base sequence. The double-stranded precursor gets loose in cancer cells to release the mature miRNA. The base sequence of the hairpin-type precursor hsa-miR-362-5p or pre-hsa-miR-362-5p may be set to generate a polynucleotide composed of the base sequence set forth in SEQ ID NO: 6 as the mature miRNA, and such a base sequence can be appropriately set by a person skilled in the art.

The hsa-miR-362-5p may be subjected to various modifications that are generally applied to nucleic acids, as necessary, to impart degradation resistance to enzyme or the like. Examples of such modifications include modification of a carbohydrate chain moiety such as 2'-O methylation; modification of a base moiety; modification of a phosphate moiety such as amination, lower alkyl amination, acetylation and the like.

(Application)

The cancer type to which the cancer therapeutic agent E is applied is esophageal cancer, pancreatic cancer, large bowel cancer, lung cancer, prostate cancer, cervical cancer, thyroid cancer, gastric cancer, liver cancer, head and neck cancer, oral cancer, or hematologic cancer (leukemia, malignant lymphoma etc.). The cancer therapeutic agent E can suppress proliferation of cancer stem cells of these cancer tissues, and thus can effectively treat these cancers.

Among the cancers to be treated with the cancer therapeutic agent E, preferably included are esophageal cancer, pancreatic cancer, large bowel cancer, gastric cancer and liver cancer.

(Administration Method)

The administration method for the cancer therapeutic agent E is not particularly limited as long as the cancer therapeutic agent E can be delivered to the tissue or cells of the cancer in vivo, but examples of the method include intravascular (intraarterial or intravenous) injection, continuous infusion, subcutaneous administration, topical administration, intramuscular administration and intraperitoneal administration. Among them, preferably included is intraarterial or intravenous administration.

The dose of the cancer therapeutic agent E is appropriately determined depending on the cancer type, the sex, age or symptom of the patient etc., so that it cannot be generally determined, but for example, in terms of the amount of mature miRNA of the hsa-miR-362-5p, about 1 to 100 mg/m$^2$ (body surface area) per day is included.

The cancer therapeutic agent E exerts a cancer therapeutic effect by the functional expression of the hsa-miR-362-5p when delivered into cells (in particular, into cancer stem cells) of the cancer. Accordingly, the cancer therapeutic agent E is desirable to be formulated with an miRNA transfer agent in order to facilitate delivery of the hsa-miR-362-5p into cancer cells. Such an miRNA transfer agent is not particularly limited, but may be any of carbonate apatite particles, Lipofectamine, Oligofectamine, RNAiFect and the like. Among these miRNA transfer agents, carbonate apatite particles can provide efficient accumulation and migration into cancer cells in vivo. Accordingly, a preferred aspect of the cancer therapeutic agent E includes those in which the hsa-miR-362-5p is present in a mixed state with a carbonate apatite particle, or the hsa-miR-362-5p is present in a complexed state with a carbonate apatite particle to form a composite particle. A description of the carbonate apatite particle used as a transfer agent for the hsa-miR-362-5p is made in the column of "8. Suitable miRNA transfer agent (carbonate apatite particle)."

7. Cancer Therapeutic Agent Using hsa-miR-608

One aspect of the present invention is a therapeutic agent for esophageal cancer, gastric cancer, pancreatic cancer, liver cancer, breast cancer, lung cancer, hematologic cancer, prostate cancer, cervical cancer, thyroid cancer, kidney cancer, head and neck cancer, oral cancer, or hematologic cancer (leukemia, malignant lymphoma etc.), the therapeutic agent containing hsa-miR-608 as an active ingredient (hereinafter, sometimes referred to as "cancer therapeutic agent F"). Hereinafter, a description is made of the cancer therapeutic agent F.

(Active Ingredient)

The hsa-miR-608 used as an active ingredient in the cancer therapeutic agent F is human-derived miR-608, the base sequence of which is as described above.

The hsa-miR-608 may be a mature miRNA, a hairpin-type precursor miRNA (pri-miRNA), or a pre-miRNA in which a part of the pri-miRNA is cleaved. The pri-miRNA or pre-miRNA is processed in cells to become the mature miRNA. In addition, the hsa-miR-608 may form a double-stranded precursor with an RNA having a complementary base sequence. The double-stranded precursor gets loose in cancer cells to release the mature miRNA. The base sequence of the hairpin-type precursor hsa-miR-608 or pre-hsa-miR-608 may be set to generate a polynucleotide composed of the base sequence set forth in SEQ ID NO: 7 as the mature miRNA, and such a base sequence can be appropriately set by a person skilled in the art.

The hsa-miR-608 may be subjected to various modifications that are generally applied to nucleic acids, as necessary, to impart degradation resistance to enzyme or the like. Examples of such modifications include modification of a carbohydrate chain moiety such as 2'-O methylation; modification of a base moiety modification of a phosphate moiety such as amination, lower alkyl amination, acetylation and the like.

(Application)

The cancer type to which the cancer therapeutic agent F is applied is esophageal cancer, gastric cancer, pancreatic cancer, liver cancer, breast cancer, lung cancer, hematologic cancer, prostate cancer, cervical cancer, thyroid cancer, kidney cancer, head and neck cancer, oral cancer, or hematologic cancer (leukemia, malignant lymphoma, etc.). The cancer therapeutic agent F can suppress proliferation of cancer stem cells of these cancer tissues, and thus can effectively treat these cancers.

Among the cancers to be treated e cancer therapeutic agent F, preferably included are esophageal cancer, gastric cancer, pancreatic cancer, liver cancer, breast cancer and lung cancer.

(Administration Method)

The administration method for the cancer therapeutic agent F is not particularly limited as long as the cancer therapeutic agent F can be delivered to the tissue or cells of the cancer in vivo, but examples of the method include intravascular (intraarterial or intravenous) injection, continuous infusion, subcutaneous administration, topical administration, intramuscular administration and intraperitoneal administration. Among them, preferably included is intraarterial or intravenous administration.

The dose of the cancer therapeutic agent F is appropriately determined depending on the cancer type, the sex, age or symptom of the patient etc., so that it cannot be generally determined, but for example, in terms of the amount of mature miRNA of the hsa-miR-608, about 1 to 100 mg/m$^2$ (body surface area) per day is included.

The cancer therapeutic agent F exerts a cancer therapeutic effect by the functional expression of the hsa-miR-608 when delivered into cells (in particular, into cancer stem cells) of the cancer. Accordingly, the cancer therapeutic agent F is desirable to be formulated with an miRNA transfer agent in order to facilitate delivery of the hsa-miR-608 into cancer cells. Such an miRNA transfer agent is not particularly limited, but may be any of carbonate apatite particles, Lipofectamine, Oligofectamine, RNAiFect and the like. Among these miRNA transfer agents, carbonate apatite particles can provide efficient accumulation and migration into cancer cells in vivo. Accordingly, a preferred aspect of the cancer therapeutic agent F includes those in which the hsa-miR-608 is present in a mixed state with a carbonate apatite particle, or the hsa-miR-608 is present in a complexed state with a carbonate apatite particle to form a composite particle. A description of the carbonate apatite particle used as a transfer agent for the hsa-miR-608 is made in the column of "8. Suitable miRNA transfer agent (carbonate apatite particle)."

8. Suitable miRNA Transfer Agent (Carbonate Apatite Particle)

Hereinafter, a description is made of the carbonate apatite panicle suitably used as an miRNA transfer agent in the agent for inhibiting proliferation of cancer stem cell and cancer therapeutic agents A to F of the present invention.

(Carbonate Apatite Particle)

Carbonate apatite is a compound having a structure in which a part of hydroxyl groups of hydroxyapatite ($Ca_{10}(PO_4)_6(OH)_2$) is replaced with $CO_3$, and thus represented by a formula $Ca_{10-m}X_m(PO_4)_6(CO_3)_{1-n}Y_n$. Here, X is an element capable of partially replacing Ca in carbonate apatite, and examples thereof include Sr, Mn and rare earth elements. m is a positive number of usually 0 or more and 1 or less, preferably 0 or more and 0.1 or less, more preferably 0 or more and 0.01 or less, still more preferably 0 or more and 0.001 or less. Y is a group or element capable of partially replacing $CO_3$ in carbonate apatite, and includes OH, F and Cl. n is a positive number of usually 0 or more and 0.1 or less, preferably 0 or more and 0.01 or less, more preferably 0 or more and 0.001 or less, still more preferably 0 or more and 0.0001 or less.

The average particle diameter of carbonate apatite particles used in the present invention is not particularly limited, as long as it has a size sufficient for administration in a living body and migration into cancer cells, but from the viewpoint of efficient accumulation and migration into cancer cells in vivo, it usually includes 50 nm or less, preferably 1 to 40 nm, more preferably 1 to 20 nm, more preferably 5 to 10 nm.

Note that the average particle diameter of carbonate apatite is a value measured by observation using a scanning probe microscope. When the particle diameter is measured with a scanning probe microscope, the measurement site is confirmed with a CCD camera. When there are huge particles (for example, a particle diameter of 5 μm or more) that are clearly unsuitable for measurement with a scanning probe microscope, they are removed from the measured target scope. In addition, in the present specification, the particle diameter means each particle diameter of independent particles that can be recognized as separate particles when measured with a scanning probe microscope. Accordingly, in a case where a plurality of particles are aggregated, the aggregate is judged as one particle.

The carbonate apatite particle can be obtained according to publicly known methods. For example, they can be obtained by preparing calcium ion, phosphate ion and bicarbonate ion in a coexistence state in an aqueous solution. The concentration of each ion in the aqueous solution is not particularly limited as long as the carbonate apatite particle is formed, but may be appropriately set with reference to the followings.

The concentration of calcium ion in the aqueous solution usually includes 0.1 to 1000 mM, preferably 0.5 to 100 mM, more preferably 1 to 10 mM.

The concentration of phosphate ion in the aqueous solution usually includes 0.1 to 1000 mM, preferably 0.5 to 100 mM, more preferably 1 to 10 mM.

The concentration of bicarbonate ion in the aqueous solution usually includes 1.0 to 10000 mM, preferably 5 to 1000 mM, more preferably 10 to 100 mM.

The supply sources of calcium ion, phosphate ion and bicarbonate ion are not particularly limited as long as these ions can be supplied in the aqueous solution, but examples thereof include water-soluble salts of these ions. Specifically, $CaCl_2$ can be used as a calcium ion source, $NaH_2PO_4 \cdot 2H_2O$ can be used as a phosphate ion source, and $NaHCO_3$ can be used as a carbonate ion source.

The aqueous solution for preparing the carbonate apatite particle may contain components other than each of the ion supply sources and other substances, as long as the carbonate apatite particle is formed. For example, fluorine ion, chlorine ion, Sr, Mn or the like may be added to the above compositions in the aqueous solution for partially replacing Ca or $CO_3$ in carbonate apatite. However, it is preferable that the added amount of fluorine ion, chloride ion, Sr or Mn be within a range that does not remarkably affect the pH solubility or the particle diameter range of the composite particle to be formed. In addition, as a base for the aqueous solution for preparing the carbonate apatite particle, water may be used, or various culture media for cell culture, buffer and the like may also be used.

In preparation of the carbonate apatite particle used in the present invention, the mixing order of each of the ion supply sources and other substances into the aqueous solution is not particularly limited, but any mixing order into the aqueous solution may be adopted for preparation as long as the desired carbonate apatite particle is obtained. For example, preparation can be performed by preparing a first solution containing calcium ion and other substances, while preparing a second solution containing phosphate ion and bicarbonate ion separately, and mixing the first solution and the second solution into the aqueous solution.

The carbonate apatite particle can be obtained by adjusting the pH of the aqueous solution containing each of the ions to a range of 6.0 to 9.0, and leaving (incubating) the aqueous solution for a certain period of time. The pH of the aqueous solution for forming the carbonate apatite particle includes, for example, 7.0 to 8.5, preferably 7.1 to 8.5, more preferably 7.2 to 8.5, still more preferably 7.3 to 8.5, particularly preferably 7.4 to 8.5, most preferably 7.5 to 8.0.

The temperature condition of the aqueous solution for forming the carbonate apatite particle is not particularly limited as long as the carbonate apatite particle is formed, but usually includes 10° C. or higher, preferably 25 to 80° C., more preferably 37 to 70° C.

The incubation time of the aqueous solution for forming the carbonate apatite particle is not particularly limited as long as the carbonate apatite particle is formed, but usually includes 1 minute to 24 hours, preferably 10 minutes to 1 hour. The presence or absence of particle formation can be confirmed, for example, by observing under a microscope.

In addition, the method for controlling the average particle diameter of the carbonate apatite particles to 50 nm or less is not particularly limited, but examples thereof include a method for subjecting the carbonate apatite particles formed in the aqueous solution to ultrasonic vibration treatment. Here, the ultrasonic vibration treatment is not a treatment in which an ultrasonic transducer such as an ultrasonic crusher or a homogenizer used for so-called bacteria cell disruption or the like is brought into direct contact with a sample to apply supersonic waves, but a treatment generally using an ultrasonic cleaner used for cleaning a precision instrument, a test tube or the like, in which cleaner an ultrasonic transducer is integrated with a cleaning tank. It means a treatment in which ultrasonication is applied through liquid to an aqueous solution containing carbonate apatite particles in the way of cleaning a precision instrument by placing the liquid (for example, water) in a cleaning tank (water tank) of a ultrasonic cleaner and floating on the liquid a container (for example, a plastic tube) containing carbonate apatite particles. In this way, the particle diameter of the carbonate apatite particles can be easily and efficiently reduced to 50 nm or less.

The apparatus usable for ultrasonic vibration treatment is not particularly limited, as long as it can indirectly apply ultrasonic vibration to a container containing carbonate apatite particles via a solvent such as water, like the above-mentioned ultrasonic cleaner. From the viewpoint of good versatility and handling property, it is preferable to use an ultrasonic cleaner provided with an ultrasonic transducer and a thermostatic bath.

The condition of the ultrasonic vibration treatment is not particularly limited as long as the particle diameter can be controlled within a predetermined range. For example, the temperature in the water tank can be appropriately selected from temperatures of 5 to 45° C., preferably 10 to 35° C., more preferably 20 to 30° C. The high frequency output of the ultrasonic vibration treatment can be appropriately set, for example, in the range of 10 to 500 W, preferably 20 to 400 W, more preferably 30 to 300 W, still more preferably 40 to 100 W. The oscillation frequency is usually 10 to 60 Hz, preferably 20 to 50 Hz, more preferably 30 to 40 Hz. The ultrasonic vibration treatment time is, for example. 30 seconds to 30 minutes, preferably 1 to 20 minutes, more preferably 3 to 10 minutes.

The type of container containing carbonate apatite particles for use in the ultrasonic vibration treatment is not limited as long as the particles can be reduced to a predetermined particle diameter range, but it can be appropriately selected depending on the volume of the aqueous solution and the purpose of use. For example, a plastic tube having a volume of 1 to 1000 ml can be used.

The ultrasonic vibration treatment is preferably performed in the presence of albumin (in other words, in a state where albumin is added to the aqueous solution containing carbonate apatite particles). This is because performing the ultrasonic vibration treatment in an environment where albumin and carbonate apatite particles coexist can provide carbonate apatite nanoparticles having more reduced particle diameter, and suppress reaggregation of the particles. The concentration of albumin in the aqueous solution containing carbonate apatite particles is not particularly limited as long as the effect of reduction and/or reaggregation suppression can be achieved, but for example, albumin can be added at 0.1 to 500 mg/ml, preferably 1 to 100 mg/ml, more preferably about 1 to 10 mg/ml.

(Composite Particle of Above-Mentioned miRNA and Carbonate Apatite Particle)

In a preferred aspect of the cancer therapeutic agents A to F and agent for inhibiting proliferation of cancer stem cell of the present invention, a composite particle is used in which the miRNA and a carbonate apatite particle are complexed. Complexing the miRNA with the carbonate apatite particle in this way can provide efficient accumulation and introduction of the miRNA into cancer cells in vivo by the action of the carbonate apatite. In addition, after introduction into cells, the miRNA can be released from the carbonate apatite particle in the cells, also making it possible to efficiently exert the antitumor effect of the miRNA.

In the present invention, the composite particle of the miRNA and the carbonate apatite particle refers to a state where the miRNA is adsorbed to and supported on the carbonate apatite particle via ionic bonding, hydrogen bonding or the like. The method for forming the composite particle of the miRNA and the carbonate apatite particle is not particularly limited, but examples thereof include a method for forming them by bringing the miRNA and a carbonate apatite particle into a coexistence state in an aqueous solution; a method by simultaneously performing formation of a carbonate apatite particle and complexation of the miRNA with the carbonate apatite particle by allowing the miRNA to coexist with calcium ion, phosphate ion and bicarbonate ion in an aqueous solution for preparing the carbonate apatite particle.

When the formation of the composite particle of the miRNA and the carbonate apatite particle is performed simultaneously with the formation of the carbonate apatite particle and the complexation of the miRNA with the carbonate apatite particle, the miRNA may be added to the aqueous solution for use in preparation of carbonate apatite at, for example, 0.1 to 1000 nM, preferably 0.5 to 500 nM, more preferably 1 to 200 nM.

In the composite particle of the miRNA and carbonate apatite particle, the ratio of the miRNA to the carbonate apatite particle is not particularly limited, but may be appropriately set depending on the dose of the miRNA etc. For example, when 2 mg of the miRNA is complexed with the carbonate apatite particle, 5 mg of the miRNA is added to 2.5 L of the aqueous solution for preparing the carbonate apatite particle to simultaneously form the carbonate apatite particle, and complex the miRNA with the carbonate apatite particle.

In addition, in the present invention, when the miRNA complexed with the carbonate apatite panicle is used, it is used in a dispersed state in a solvent suitable for administration to a living body. As described above, the carbonate apatite particle is obtained by dissolving substances to become various ion supply sources in the solvent such as water, culture medium or buffer, but the carbonate apatite particle dispersion solution obtained in this way is not always suitable for administration to a living body (intravascular administration) from the viewpoint of osmotic pressure, buffering capacity, sterility, etc. Accordingly, in order to replace the solvent in which the carbonate apatite particles are dispersed with a solvent suitable for administration to a living body (for example, physiological saline), an operation is usually required to separate and recover the carbonate apatite particles from the solvent by centrifugation for the replacement of the solvent. However, when such an operation is performed, the carbonate apatite particles are aggregated with each other to enlarge particles, so that the state of the particles is unfortunately changed to a state unsuitable for administration to a living body. Accordingly, adding the aggregated carbonate apatite particles to a solvent suitable for administration to a living body, and also performing the ultrasonic vibration treatment allow the composite particles of the miRNA and the carbonate apatite particle to disperse in the solvent suitable for administration to a living body with an appropriate particle diameter (preferably, an average particle diameter of 50 nm or less).

In addition, in the cancer therapeutic agents A to F and agent for inhibiting proliferation of cancer stem cell of the present invention, when the miRNA complexed with the carbonate apatite particle is used, administration of the cancer therapeutic agents A to F and agent for inhibiting proliferation of cancer stem cell of the present invention is desirable to be performed immediately after dispersing the composite particles of the miRNA and the carbonate apatite particle in a state of fine particles by ultrasonic vibration treatment before the particles aggregate. For example, administration within 1 minute, preferably within 30 seconds after ultrasonic vibration treatment is suitable. However, as described above, when suppressing aggregation of the carbonate apatite particles by adding albumin, administration may also be performed several minutes to several tens of minutes after ultrasonic vibration treatment.

EXAMPLES

Hereinafter, a description is made of the present invention with reference to Examples. However, the present invention is not to be construed as being limited to the following Examples.

Test Example 1

Screening of Nucleic Acid (miRNA)

1. Test Material
1-1. Preparation of Cancer Stem Cell
1-1-1. Establishment of Cancer Stem Cell A cancer stem cell line was established by transducing a pancreatic cancer cell line (Panc-1) with an ODC (Ornithine Decarboxylase)-Degron system capable of visualizing low metabolism that is a property of cancer stem cells using a retrovirus vector (FIG. 1a). The base sequence coding the used ODC-Degron is as set forth in SEQ ID NO: 10. Usually, cancer stem cells are so 26s proteasome hypometabolic that they cannot degrade the introduced fluorescently labeled Ornithine Decarboxylase Degron, and thus the fluorescent protein sufficiently accumulates to provide visualization.

However, even when the ODC-degron system was introduced into the pancreatic cancer cell line Panc-1, only about 0.06% cells emitting fluorescence (green) were obtained in total. With such a small number of cancer stem cells, a series of experiments including drug screening cannot be performed. Accordingly, further enrichment of cancer stem cells provided a cancer stem cell population in which cells having observed fluorescent coloring (i.e., cancer stem cells) accounted for about 81.18% in total (FIG. 1b). The obtained cancer stem cell population was designated as ZsGreen+.

1-1-2. Characterization of Established Cancer Stem Cell

As to the obtained cancer stem cell population (Zs-Green+), in order to confirm the characteristics of the cancer stein cells, the ability to form spheres, anticancer drug resistance, ability to express a stein cell marker, and asymmetric division potency were confirmed. For comparison, a non-cancerous stem cell population (ZsGreen−) that was obtained through introduction of the ODC-degron system into the pancreatic cancer cell line Panc-1 and did not emit fluorescence was also subjected to characterization in the same way.

As to the ability to form spheres, using 96-well Ultra Low Cluster Plate, each cell population was seeded at 100 to 3000 cells/well and cultured at 37° C. in (DMEM) medium, and then the state of cell was observed over 2 weeks for confirmation.

As to the anticancer drug resistance, using a 96-well plate, each cell population was seeded at 5000 to 10000 cells/well and cultured at 37° C. for 2 to 4 days in a medium (DMEM medium containing 10% by volume FBS) supplemented with 2 or 5 µM oxaliplatin (L-OHP), and then the number of living cells were counted to determine the cell viability (%).

As to the expression of stem cell marker, expression of stem cell markers Bmi1 and CD44v9, and a cancer stem cell-specific marker Dclk1 was measured by qPCR and Western blotting. The expression levels of Bmi1 and Dclk1 were corrected with the expression level of the housekeeping gene (GAPDH), and the expression level of CD44v9 was corrected with the expression level of the housekeeping gene (Actin).

As to the asymmetric division potency, using ibidi 35 mm Plate, each cell population was seeded at 1000 to 10000 cells/plate and cultured at 37° C. for 1 day in a medium (DMEM medium containing 10% by volume FBS), and then the condition of cells was continuously observed over 1 week for confirmation. Note that cancer stem cells have the property of asymmetrically dividing to produce daughter cells having different properties, resulting in genetically heterogeneous cell division.

Figure 2:
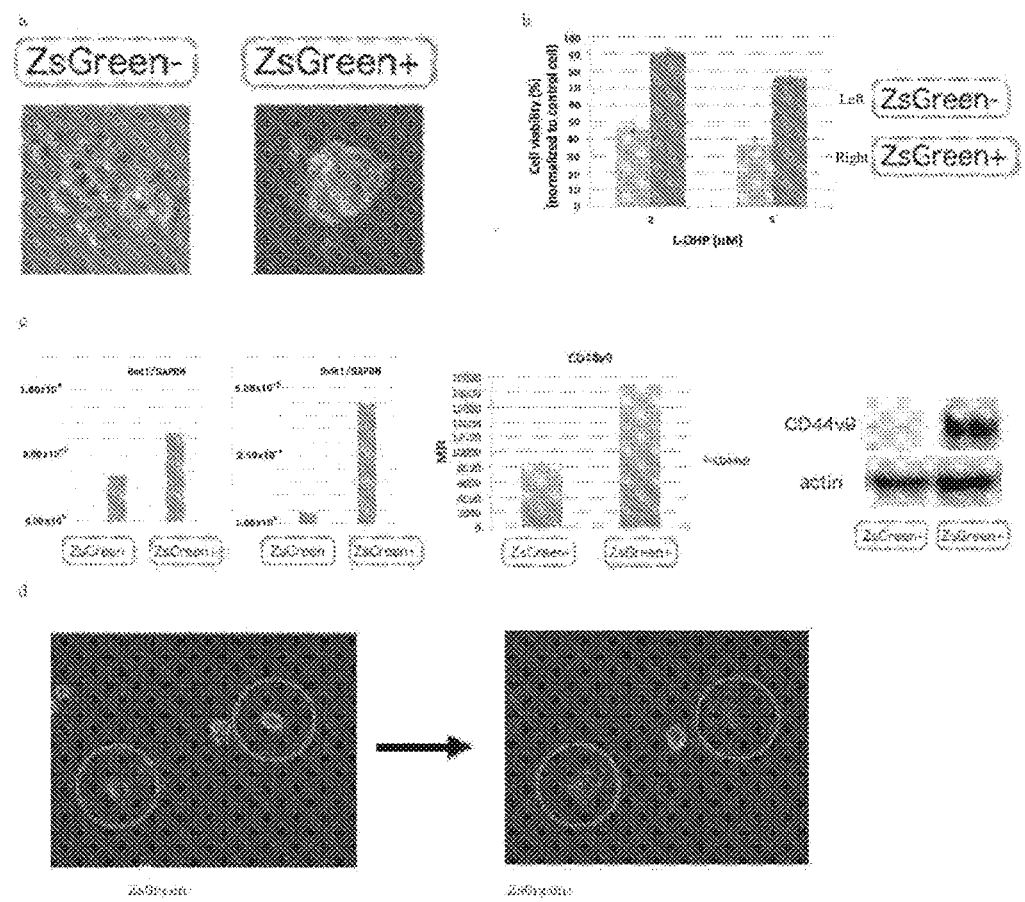
FIG. 2 shows the result of confirmation of the presence or absence of characteristics of cancer stem cells for a cancer stem cell population (ZsGreen+, an established cancer stem cell population) and a non-cancer stem cell population (ZsGreen−, negative control). The result of evaluation of the ability to form spheres is shown in FIG. 2a, the result of evaluation of the anticancer drug resistance in FIG. 2b, the result of evaluation of the ability to express a stem cell marker in FIG. 2c, and the result of evaluation of the asymmetric division potency in FIG. 2d.

In FIG. 2, the result of confirmation of the presence or absence of characteristics of cancer stein cells is shown for the cancer stem cell population (ZsGreen+) and the non-cancer stem cell population (ZsGreen−, negative control). In FIG. 2, the result of evaluation of the ability to form spheres is shown in a, the result of evaluation of the anticancer drug resistance in b, the result of evaluation of the ability to express a stem cell marker in c, and the result of evaluation of the asymmetric division potency in d. As a result, the cancer stem cell population (ZsGreen+) has an ability to form spheres, anticancer drug resistance and symmetric division potency, and observed expression of the stem cell markers and the cancer stem cell-specific marker, confirming that the population has characteristics of cancer stem cells.

1-1-3. Analysis of Tumorigenicity of Established Cancer Stem Cell

Following tests were performed to confirm the tumorigenicity of the obtained cancer stem cell population (Zs-Green+). First, subcutaneous transplantation of the cancer stem cell population (ZsGreen+) was performed to 6 to 8 weeks old SCID beige mice (n=3) so as to provide 150 cells each. Six weeks later, the site where the cells were transplanted was observed to confirm the presence or absence of tumor formation. For comparison, also for the non-cancer stem cell population (ZsGreen−), the tumorigenicity was analyzed in the same way.

Figure 3:
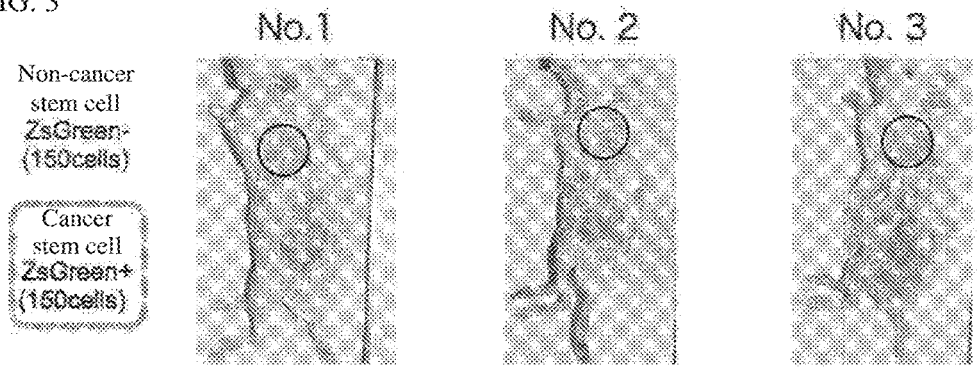
FIG. 3 is the result of observation of transplanted sites on mouse 6 weeks after 150 cells from a cancer stem cell population (ZsGreenH+) and 150 cells from a non-cancer stem cell population (ZsGreen−) are each subcutaneously transplanted.

The obtained result is shown in FIG. 3. As a result, the transplantation of only 150 cells from the cancer stein cell population (ZsGreen+) successfully formed tumor, making it clear that the tumorigenicity is high. On the other hand, the transplantation of 150 cells from the non-cancer stem cell population (ZsGreen−) failed to form a tumor.

1-2. Selection of Candidate miRNA miRNAs that can act on DCLK1, a gene specifically expressed in cancer stem cells, were subjected to in silico analysis to select 32 candidate miRNAs. Furthermore, 35 miRNAs out of 800 miRNAs were selected by nCounter miRNA expression array of the non-cancer stem cell population (ZsGreen−) and cancer stem cell population (ZsGreen+). A total of these 67 miRNAs were subjected to the screening described below. Note that all miRNAs subjected to the screening are mature miRNAs.

2. Screening Method

A cell suspension prepared by suspending the cancer stem cell population (ZsGreen+) in a medium (DMEM medium containing 10% by volume FBS) was seeded in each well of a 24-well plate at a density of 5000 to 10000 cells/well, followed by culture at 37° C. overnight. Thereafter, according to the lipofectamin 2000 protocol, each miRNA was transfected at 10 pmol/well, and 48 hours and 72 hours later, the cells were counted. In addition, tests were also conducted under the same condition on a case where the miRNA was not introduced (untreated group, control), a case where has-miR-34a (SEQ ID NO: 8) was used (positive control) in place of the selected miRNA, and a case where a control miRNA (SEQ ID NO: 9) was used (NC1, negative control) in place of the selected miRNA. In addition, for comparison, the non-cancer stem cell population (ZsGreen−) was used in place of the cancer stem cell population (ZsGreen+) to conduct tests under the same condition.

The ratio of the number of cells under each condition to the number of control cells into which the miRNA was not introduced (cell viability, %) was determined.

3. Result

Figure 4:
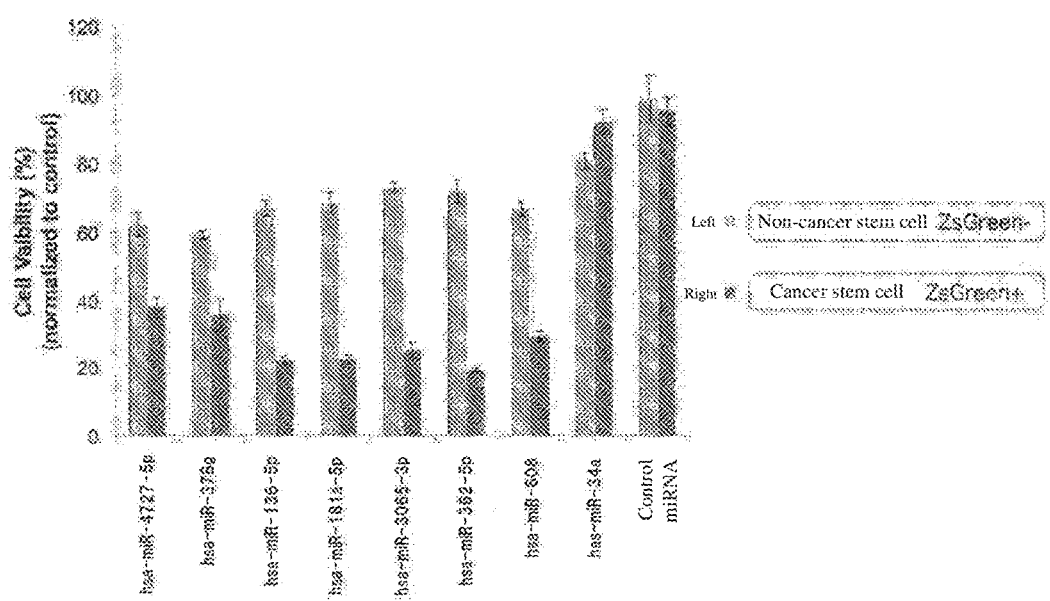
FIG. 4 shows the result of screening of miRNAs capable of effectively suppressing proliferation of cancer stem cells.

As a result of the screening, as miRNAs that can effectively suppress proliferation of cancer stem cells, seven miRNAs (hsa-miR-136-5p, hsa-miR-3065-3p, hsa-miR-4727-5p, hsa-miR-378g, hsa-miR-181a-5p, hsa-miR-362-5p and hsa-miR-608) have been found. Among these seven miRNAs, hsa-miR-136-5p, hsa-miR-181a-5p, hsa-miR-3065-3p, hsa-miR-362-5p and hsa-miR-608 had prominent proliferation inhibitory effect on cancer stem cells. FIG. 4 shows the cell viability when these seven miRNAs are used. On the other hand, in the case of has-miR-34a, which is conventionally considered to have the highest therapeutic effect on solid tumor, the proliferation inhibitory effect on cancer stem cells was not sufficient (FIG. 4).

The seven miRNAs were superior in terms of cancer stem cell proliferation inhibition, but the degree of non-cancer stem cell proliferation inhibition was only slightly higher than that of has-miR-34a. From the result, it has been clear that the seven miRNAs can effectively suppress proliferation of both of the cancer stein cells and non-cancer stem cells using another anticancer drug in combination, and thus exert a superior therapeutic effect on cancer.

Test Example 2

Evaluation of Antitumor Effect of hsa-miR-136-5p in Mouse Subcutaneous Solid Tumor Model 1. Production of Composite Particle of miRNA and Carbonate Apatite In 100 ml of distilled water, 0.37 g of $NaHCO_3$, 90 μl of $NaH_2PO_4.2H_2O$ (1M) and 180 μl of $CaCl_2$ (1 M) were added in this order and dissolved, and the pH was adjusted to 7.5 with 1N HCl. This was filtered through 0.2 μm diameter filter. Per 1 ml of the resultant buffer, 2 μg of miRNA and 4 μl of $CaCl_2$ (1 M) were mixed and incubated in a water bath at 37° C. for 30 minutes. Then, spin down was performed at 15000 rpm×5 minutes. The resultant pellet was dispersed in physiological saline (containing 0.5 wt % albumin). Accordingly, a dispersion of composite particles containing the miRNA in carbonate apatite particles was obtained. The resultant dispersion was subjected to ultrasonic vibration treatment for 10 minutes just prior to testing. Note that the ultrasonic vibration treatment was performed for 10 minutes using a water bath with an ultrasonic vibration function, in which the dispersion contained in a plastic container was floated on water set to 20° C., under conditions of high frequency output of 55 W and oscillation frequency of 38 kHz. The preparation obtained in this way was immediately used for the tests described below.

Note that it is confirmed in the measurement using a scanning probe microscope that the dispersion of ultrasonic vibration treatment includes composite particles composed of carbonate apatite nanoparticles containing the miRNA having an average particle diameter of 50 nm or less. It is also confirmed that the resultant composite particles contain about 20 μg of the miRNA per 1 mg of carbonate apatite.

2. Mouse Subcutaneous Solid Tumor Model Test

The cancer stem cell population (ZsGreen+) obtained in Test Example 1 was subcutaneously injected at $5 \times 10^5$ cells to the left and right backs of 6 to 8 weeks age BALB/cA nude mice (manufactured by CLEA Japan, Inc.) to produce solid tumor model mice. When the tumor reached about 20 $mm^3$ in size, the mice were randomly divided into an hsa-miR-136-5p administration group (hsa-miR-136-5p), an untreated group, and a negative control group (control miRNA). In the hsa-miR-136-5p administration group, the day at which the tumor reached about 20 $mm^3$ in size was 0th day. On the 0th, 3rd, 5th, 7th, 10th, 12th, 14th, 17th and 19th days, carbonate apatite nanoparticles containing the hsa-miR-136-5p were intravenously injected into the tail vein at 40 μg/dose in terms of the amount of hsa-miR-136-5p. In the negative control group, carbonate apatite nanoparticles containing a control miRNA (SEQ ID NO: 9) were intravenously injected into the tail vein at the same schedule and dose as those for the miRNA136-5p administration group. In the untreated group, no drug was administered. During the test period, the tumor volume on the back of the mouse (longer diameter×shorter diameter×shorter diameter× 1/2) was measured over time, and on the 24th day, the tumor was excised from the mice and observed for size, and its weight was measured.

3. Result

Figure 5:
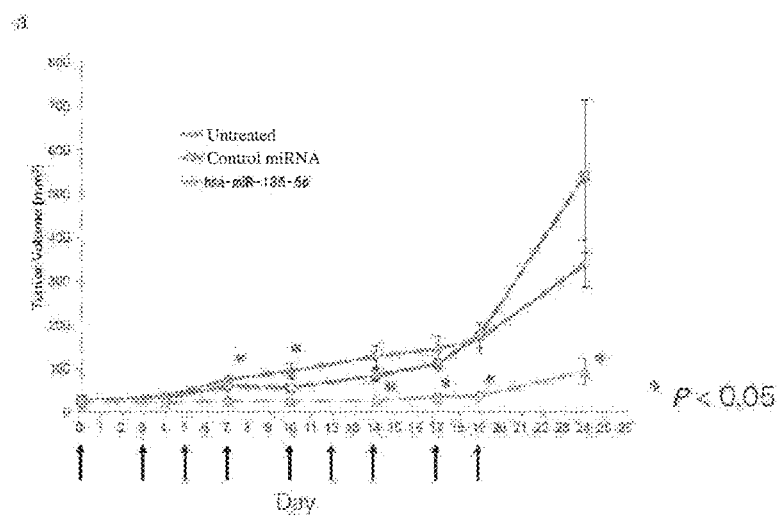
FIG. 5 is the result of evaluation of the antitumor effect of hsa-miR-136-5p in a mouse subcutaneous solid tumor model.
Figure 5:
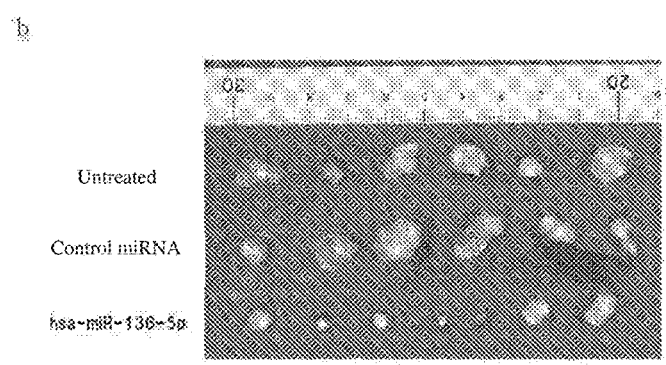
Figure 5:
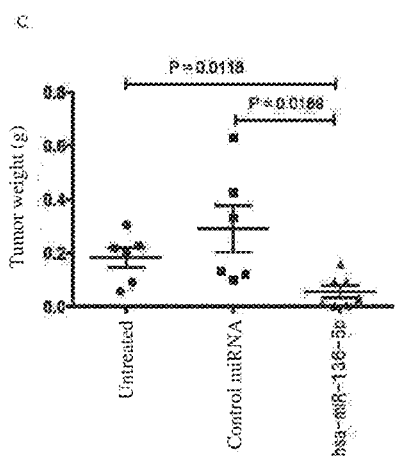

The obtained result is shown in FIG. 5. In FIG. 5, in a, the result of the tumor volume measured over time is shown, in b, the result of observation of the tumor excised from the mice on the 24th day is shown, and in c, the result of the measured weight of the tumor removed from the mice on the 24th day is shown. From these results, a remarkably higher antitumor effect was observed in the hsa-miR-136-5p administration group as compared to the untreated group and the negative control group (control miRNA). In particular, after the 7th day, the hsa-miR-136-5p administration group had a significantly smaller tumor volume, as compared to the untreated group and the negative control group (FIG. 5*a*). In addition, the tumor excised on the 24th day was significantly smaller in the hsa-miR-136-5p administration group, as compared to the untreated group and the negative control group (FIGS. 5*b* and 5*c*).

Test Example 3

Evaluation of Antitumor Effect of hsa-miR-3065-3p in Mouse Subcutaneous Solid Tumor Model A mouse subcutaneous solid tumor model test was conducted in the same manner as in Test Example 2 except that hsa-miR-3065-3p was used in place of hsa-miR-136-5p.

Figure 6:
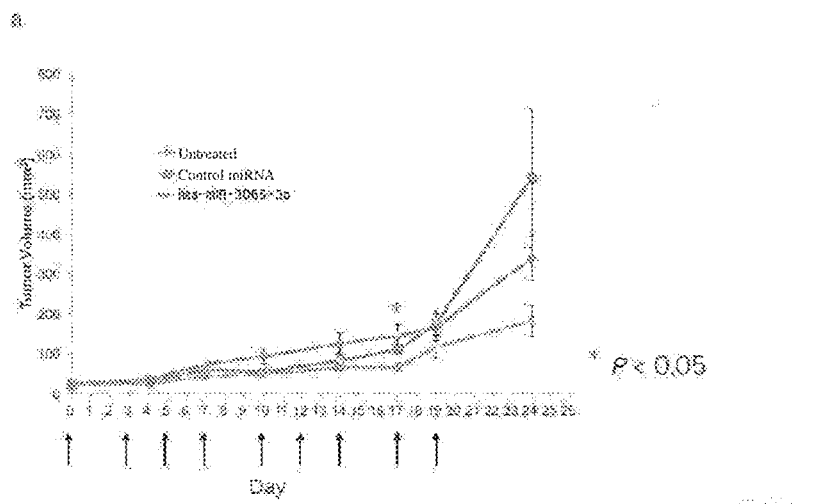
FIG. 6 is the result of evaluation of the antitumor effect of hsa-miR-3065-3p in a mouse subcutaneous solid tumor model.
Figure 6:
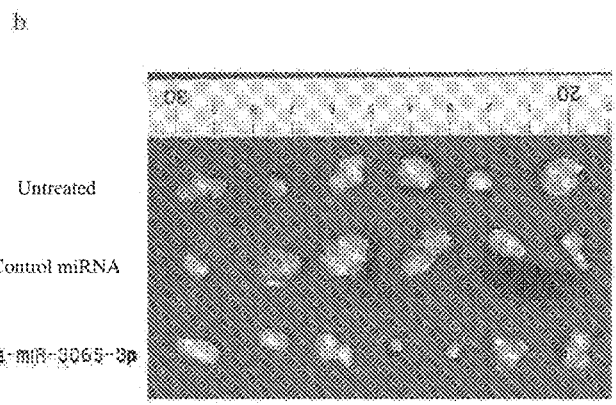

The obtained result is shown in FIG. 6. In FIG. 6, in a, the result of the tumor volume measured over time is shown, and in b, the result of observation of the tenor excised from the mice on the 24th day is shown. From these results, it was confirmed that in the hsa-miR-3065-3p administration group, the tumor volume was significantly reduced from the 17th day as compared to the untreated group and the negative control group (control miRNA).

Test Example 4

Evaluation of Antitumor Effect of hsa-miR-181-5p in Mouse Subcutaneous Solid Tumor Model A mouse subcutaneous solid tumor model test was conducted in the same manner as in Test Example 2 except that hsa-miR-181-5p was used in place of hsa-miR-136-5p.

Figure 7:
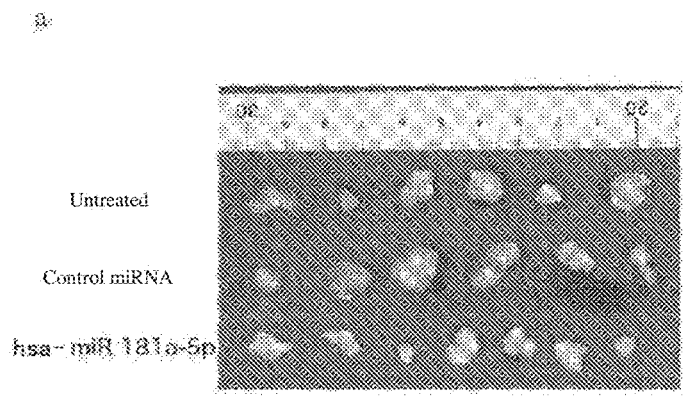
FIG. 7 is the result of evaluation of the antitumor effect of hsa-miR-181-5p in a mouse subcutaneous solid tumor model, showing the result of observation of the tumor excised on the 24th day.

The result of the observed tumor excised from the mice on the 24th day is shown in FIG. 7. From the result, a remarkably higher antitumor effect was observed in the hsa-miR-181-5p administration group as compared to the untreated group and the negative control group (control miRNA).

Test Example 4

Evaluation of Antitumor Effect on Human Pancreatic Cancer Cell (1)

As to hsa-miR-136-5p, hsa-miR-3065-3p, hsa-miR-4727-5p, hsa-miR-378g and hsa-miR-181a-5p, evaluation was performed of the antitumor effect on human pancreatic cancer cells. The specific test method is as follows.

A cell suspension prepared by suspending human pancreatic cancer cells (Bxpc3 line) in D-MEM medium (containing 10% by volume FBS) was seeded in each well of a 24-well plate at $3 \times 10^3$ cells/well, followed by culture at 37° C. overnight. Thereafter, according to the lipofectamin 2000 protocol, each miRNA was transfected at 10 pmol/well, and 48 hours later, the cells were counted. In addition, tests were also conducted under the same condition on a case where the miRNA was not introduced (untreated group), a case where hsa-miR-34a (SEQ ID NO: 8) was used (positive control) in place of the miRNA, and a case where a control miRNA (SEQ ID NO: 9) was used (control miRNA, negative control) in place of the selected miRNA.

Figure 8:
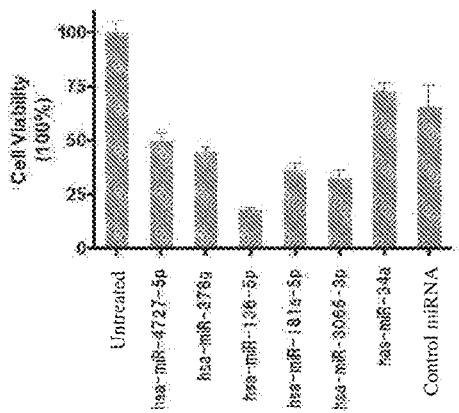
FIG. 8 is the result of evaluation of the proliferation inhibitory effects of hsa-miR-136-5p, hsa-miR-3065-3p, hsa-miR-4727-5p, hsa-miR-378g and hsa-miR-181a-5p using human pancreatic cancer cells (Bxpc3 line).

The obtained result is shown in FIG. 8. From the result, it was observed that hsa-miR-136-5p, hsa-miR-3065-3p, hsa-miR-4727-5p, hsa-miR-378g and hsa-miR-181a-5p had a strong proliferation inhibitory effect on pancreatic cancer cells, and a much better antitumor effect than that of hsa-miR-34a. In particular, for hsa-miR-136-5p, a particularly remarkable antitumor effect was observed. This is because, among pancreatic cancer cells (Bxpc3 line cancer stem cells are present, so that the miRNAs are considered to intensively suppress proliferation of the cancer stem cells in particular, thereby suppressing proliferation of pancreatic cancer cells as a whole.

Test Example 5

Evaluation of Antitumor Effect on Human Pancreatic Cancer Cell (2)

As to hsa-miR-136-5p, hsa-miR-3065-3p and hsa-miR-181a-5p, evaluation was performed of the antitumor effect on human pancreatic cancer cells. The specific test method is the same as that for Test Example 4 except that a PSN-1 line was used as human pancreatic cancer cells.

Figure 9:
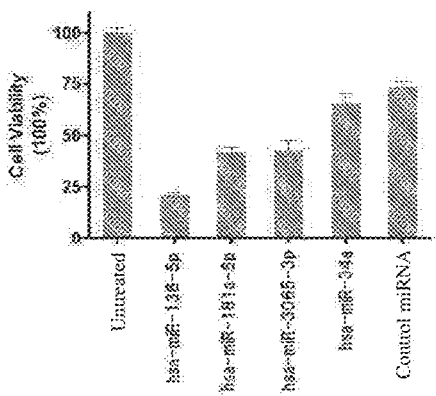
FIG. 9 is the result of evaluation of the proliferation inhibitory effects of hsa-miR-136-5p, hsa-miR-3065-3p and hsa-miR-181a-5p using human pancreatic cancer cells (PSN-1 line).

The obtained result is shown in FIG. 9. Also from this result, it was confirmed that hsa-miR-136-5p, hsa-miR-3065-3p and hsa-miR-181a-5p had a strong proliferation inhibitory effect on pancreatic cancer cells. In particular, for hsa-miR-136-5p, a particularly remarkable antitumor effect was observed. This is because, among pancreatic cancer cells (PSN-1 line), cancer stem cells are present, so that the miRNAs are considered to intensively suppress proliferation of the cancer stem cells in particular, thereby suppressing proliferation of pancreatic cancer cells as a whole.

Test Example 6

Evaluation of Antitumor Effect on Human Gastric Cancer Cell

As to hsa-miR-136-5p, hsa-miR-3065-3p and hsa-miR-181a-5p, evaluation was performed of the antitumor effect on human gastric cancer cells. The specific test method is the same as that for Test Example 4 except that human gastric cancer cells (AGS line) were used as cancer cells.

Figure 10:
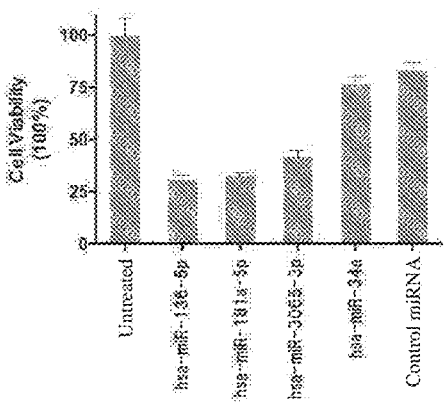
FIG. 10 is the result of evaluation of the proliferation inhibitory effects of hsa-miR-136-5p, hsa-miR-3065-3p and hsa-miR-181a-5p using human gastric cancer cells (AGS line).

The obtained result is shown in FIG. 10. From the result, it was observed that hsa-miR-136-5p, hsa-miR-3065-3p and hsa-miR-181a-5p had a strong proliferation inhibitory effect on gastric cancer cells, and a much better antitumor effect than that of hsa-miR-34a. In particular, for hsa-miR-136-5p and hsa-miR-181a-5p, a particularly remarkable antitumor effect was observed. This is because, among gastric cancer cells (AGS line), cancer stem cells are present, so that the miRNAs are considered to intensively suppress proliferation of the cancer stem cells in particular, thereby suppressing proliferation of gastric cancer cells as a whole.

Test Example 7

Evaluation of Antitumor Effect on Human Large Bowel Cancer Cell

As to hsa-miR-136-5p, hsa-miR-3065-3p, hsa-miR-4727-5p, hsa-miR-378g, hsa-miR-181a-5p, hsa-miR-362-5p and hsa-miR-608, evaluation was performed of the antitumor effect on human large bowel cancer cells. The specific test method is the same as that for Test Example 4 except that human large bowel cancer cells (DLD1 line) were used as cancer cells, and that the cells were counted 72 hours after transfection.

Figure 11:
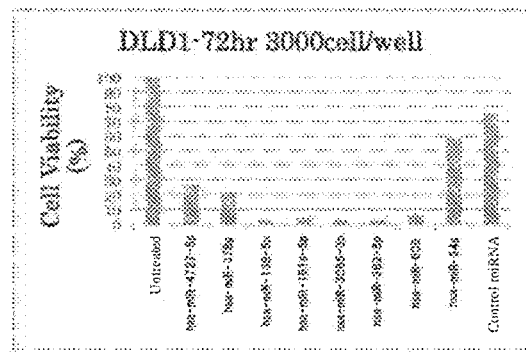
FIG. 11 is the result of evaluation of the proliferation inhibitory effects of hsa-miR-136-5p, hsa-miR-3065-3p, hsa-miR-4727-5p, hsa-miR-378g, hsa-miR-181a-5p, hsa-miR-362-5p and hsa-miR-608 using human large bowel cancer cells (DLD1 line).

The obtained result is shown in FIG. 11. From this result, it was observed that hsa-miR-136-5p, hsa-miR-3065-3p, hsa-miR-4727-5p, hsa-miR-378g, hsa-miR-181a-5p, hsa-miR-362-5p and hsa-miR-608 had a strong proliferation inhibitory effect on large bowel cancer cells, and a much better antitumor effect than that of hsa-miR-34a. In particular, it was observed that hsa-miR-136-5p, hsa-miR-3065-3p, hsa-miR-181a-5p, hsa-miR-362-5p and hsa-miR-608 had a particularly remarkable antitumor effect. This is because, among large bowel cancer cells (DLD1 line), cancer stem cells are present, so that the miRNAs are considered to intensively suppress proliferation of the cancer stem cells in particular, thereby suppressing proliferation of large bowel cancer cells as a whole.

Test Example 8

Evaluation of Antitumor Effect on Human Esophageal Cancer Cell

As to hsa-miR-136-5p, hsa-miR-3065-3p, hsa-miR-4727-5p, hsa-miR-378g and hsa-miR-181a-5p, evaluation was performed of the antitumor effect on human esophageal cancer cells. The specific test method is the same as that for Test Example 4 except that human esophageal cancer cells (TE11 line) were used as cancer cells, and that the cells were counted 72 hours after transfection.

Figure 12:
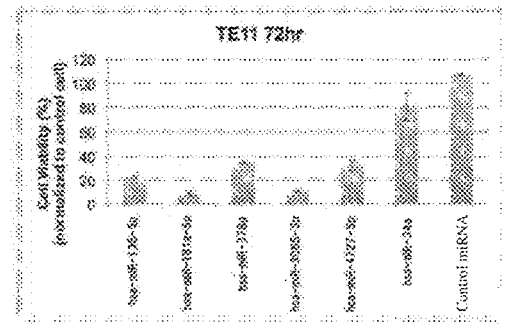
FIG. 12 is the result of evaluation of the proliferation inhibitory effects of hsa-miR-136-5p, hsa-miR-3065-3p, hsa-miR-4727-5p, hsa-miR-378g and hsa-miR-181a-5p using human esophageal cancer cells (TE11 line).

The obtained result is shown in FIG. 12. From the result, it was observed that hsa-miR-136-5p, hsa-miR-3065-3p, hsa-miR-4727-5p, hsa-miR-378g and hsa-miR-181a-5p had a strong proliferation inhibitory effect on esophageal cancer cells, and a much better antitumor effect than that of hsa-miR-34a. In particular, for hsa-miR-3065-3p and hsa-miR-181a-5p, a particularly remarkable antitumor effect was observed. This is because, among esophageal cancer cells (TE11 line), cancer stem cells are present, so that the miRNAs are considered to intensively suppress proliferation of the cancer stem cells in particular, thereby suppressing proliferation of esophageal cancer cells as a whole.

Test Example 9

Evaluation of Proliferation Inhibitory Effect on Human Large Bowel Cancer Cell

Proliferation assay was performed on human large bowel cancer cells using hsa-miR-3065-3p. The specific test method is as follows.

A cell suspension prepared by suspending human large bowel cancer cells (HT29 line, HCT116 line and DLD1 line) in DMEM medium (containing 10% by volume FBS) was seeded in each well of a 96-well plate at $3 \times 10^3$ cells/well, followed by culture at 37° C. overnight. Then, a mixture of lipofectamin RNAiMAX, Reagent (final concentration in each well: 0.03 μL/ml) and hsa-miR-3065-3p (final concentration in each well: 50 nM) was added for transfection. Subsequently, culture was carried out for 96 hours, and the absorbance at 450 nm was measured over time. In addition, tests were also performed wider the same condition on a case where a control miRNA (SEQ ID NO: 9) was used (control miRNA, negative control) in place of hsa-miR-3065-3p.

Figure 13:
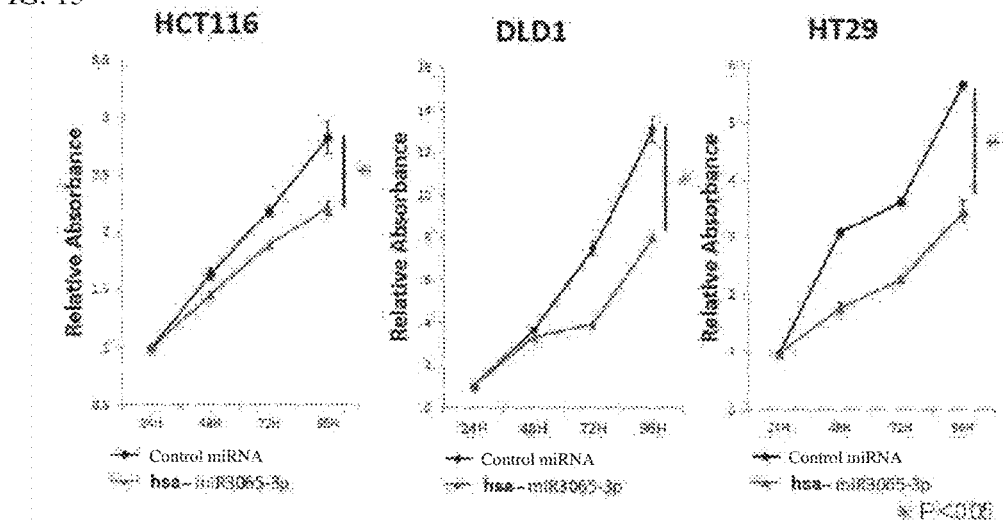
FIG. 13 is the result of proliferation assay performed on human large bowel cancer cells (HT29 line, HCT116 line and DLD1 line) using hsa-miR-3065-3p.

The obtained result is shown in FIG. 13. In FIG. 13, the time-course of relative values of the absorbance is shown, in which the relative values were determined when the absorbance after culture for 24 hours from transfection of hsa-miR-3065-3p was 1. From the result, it was confirmed that hsa-miR-3065-3p had a high proliferation inhibitory effect on human large bowel cancer cells. This is because, as described above, among human large bowel cancer cells (HT29 line, HCT116 line and DLD1 line), cancer stem cells are present, so that hsa-miR-3065-3p is considered to intensively suppress proliferation of the cancer stem cells in particular, leading to the result.

Test Example 10

Evaluation of Ability to Inhibit Colonization of Human Large Bowel Cancer Cell

Colony formation assay was performed on human large bowel cancer cells using hsa-miR-3065-3p. The specific test method is as follows.

A cell suspension prepared by suspending human large bowel cancer cells (DLD1 line and HT29 line) in RPMI medium (containing 10% by volume FBS) was seeded in each well of a 6-well plate at $3\times10^5$ cells/well, followed by culture for 2 days. Then, the medium was changed to RPMI medium (containing no FBS), and a mixture of lipofectamin RNAiMAX Regent (final concentration in each well: 0.03 µL/ml) and hsa-miR-3065-3p (final concentration in each well: 50 nM) was added for transfection, followed by culture for 8 hours. Then, cells after transfection were recovered and suspended in RPMI medium (containing 10% by volume FBS), and were seeded in each well of a 6-well plate at 500 cells/well, followed by culture for 10 days. Thereafter, the culture supernatant was removed, and cells were fixed with methanol and then stained with crystal violet to count the formed colonies. In addition, tests were also performed under the same condition on a case where a control miRNA (SEQ ID NO: 9) was used (control miRNA, negative control) in place of hsa-miR-3065-3p.

Figure 14:
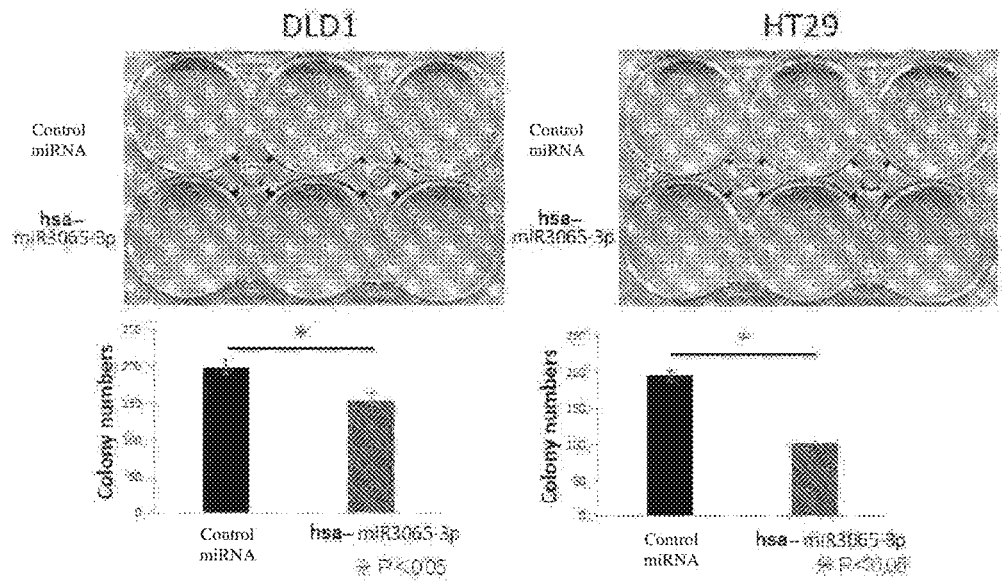
FIG. 14 is the result of colony formation assay performed on human large bowel cancer cells (DLD1 line and HT29 line) using hsa-miR-3065-3p.

The obtained result is shown in FIG. 14. From the result, it was confirmed that hsa-miR-3065-3p was able to inhibit the colony forming ability of human large bowel cancer cells.

Test Example 11

Evaluation of Ability to Inhibit Migration of Human Large Bowel Cancer Cell

Infiltration assay was performed on human large bowel cancer cells using hsa-miR-3065-3p. The specific test method is as follows.

The infiltration assay was performed using BD Matrigel Invasion Chambers, 12 Chambers per 24-Well Plate (BD Biosciences). First, 650 ml of RPMI medium (containing 10% by volume FBS) was added in the wells of a companion plate. Furthermore, in a cell culture insert having a Matrigel basement membrane, a mixture of human large bowel cancer cells (DLD1 line) at $1\times10^6$ cells/well, lipofectamin RNAiMAX Regent (final concentration in the cell culture insert: 2 µL/ml) and hsa-miR-3065-3p (final concentration in the cell culture insert: 20 pmol/cell culture insert) was added, followed by culture for 48 hours. Thereafter, the cell culture insert was removed, and cells adhering to the outside of the Matrigel basement membrane were fixed with formalin and then stained with hematoxylin to count the cells migrated to the outside of the Matrigel basement membrane. In addition, tests were also performed under the same condition on a case where a control miRNA (SEQ ID NO: 9) was used (control miRNA, negative control) in place of hsa-miR-3065-3p.

Figure 15:
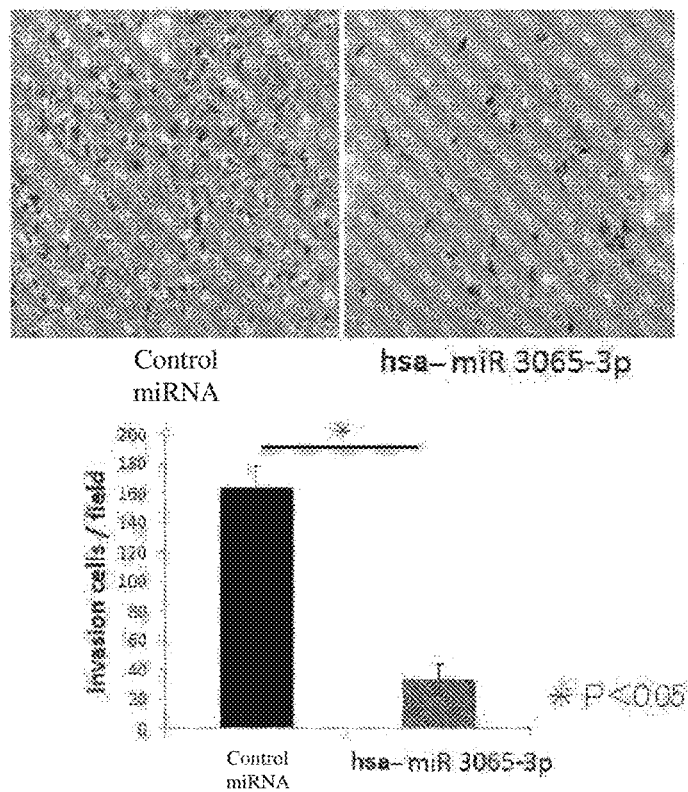
FIG. 15 is the result of infiltration assay performed on human large bowel cancer cells (DLD1 line) using hsa-miR-3065-3p.

The obtained result is shown in FIG. 15. From the result, it was confirmed that hsa-miR-3065-3p was able to inhibit the migration ability of human large bowel cancer cells.

Test Example 11

Evaluation of Drug Sensitivity of Human Large Bowel Cancer Cell in Combination with Anticancer Drug The drug sensitivity of human large bowel cancer cells was evaluated using hsa-miR-3065-3p and oxaliplatin (L-OHP). The specific test method is as follows.

A cell suspension prepared by suspending human large bowel cancer cells (HT29 line) in RPMI medium was seeded in each well of a 6-well plate at $3\times10^5$ cells/well, and a mixture of lipofectamin RNAiMAX Regent (final concentration in well: 0.03 µL/well) and hsa-miR-3065-3p (final concentration in well: 50 nM) was further added, followed by culture for 1 day. Then, cells were recovered and suspended in RPMI medium, and were seeded in each well of a 96-well plate at $3\times10^3$ cells/well, followed by culture for 2 days. Thereafter, oxaliplatin was added to each well at 0, 2, 4, 8, 16, 32, 64 or 128 µM, followed by additional culture for 72 hours. After culture, living cells in each well were counted by GloMax-Multi Detection System (Promega Corporation). When the number of living cells under a condition where oxaliplatin was not added was 100%, the ratio of the number of living cells under each condition (cell viability, %) was determined. In addition, tests were also performed under the same condition on a case where a control miRNA (SEQ ID NO: 9) was used (control miRNA, negative control) in place of hsa-miR-3065-3p, and on a case where no miRNA was added.

Figure 16:
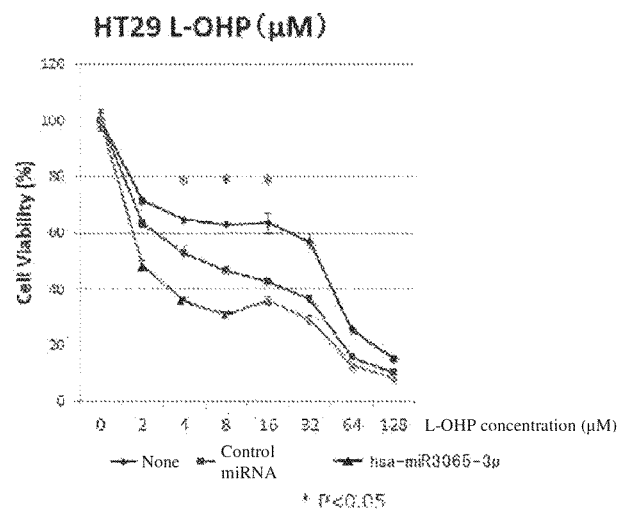
FIG. 16 is the result of evaluation of drug sensitivity to human large bowel cancer cells (HT29 line) using hsa-miR-3065-3p and oxaliplatin.

The obtained result is shown in FIG. 16. From the result, a treatment with both hsa-miR-3065-3p and oxaliplatin was able to significantly reduce the number of living cells of human large bowel cancer cells, compared to a treatment with only oxaliplatin and a treatment with both control and oxaliplatin. In other words, from the result, it is considered that hsa-miR-3065-3p was able to effectively suppress proliferation of cancer stem cells, and oxaliplatin was able to suppress proliferation of cancer cells other than cancer stem cells, thereby drastically reducing the total number of cancer cells.

Test Example 12

Evaluation of Migration of Human Large Bowel Cancer Cell

Wound healing assay was performed using hsa-miR-3065-3p and human large bowel cancer cells. The specific test method is as follows.

Wound healing assay was performed using Culture-Insert (NIPPON Genetics Co, Ltd). In each well of a 24-well plate, 70 µl of cell suspension ($4.9\times10^4$ cells/well) prepared by suspending human large bowel cancer cells (DLD1 line) in RPMI medium (containing 10% by volume FBS) and an insert that could create a constant gap of 0.5±0.05 mm in width between cells were placed, followed by culture for 1 day, so that a single layer of cells and an area where there is no cell (wound area) corresponding to the gap were formed at the bottom of the well. Then, the insert and culture supernatant were remove, 500 μl of DMEM medium (serum free) was added to each well, and further a mixture of lipofectamin RNAiMAX Regent (final concentration in well: 2 μl/well) and hsa-miR-3065-3p (final concentration in well: 20 pmol/well) was added, followed by culture for 1 day. Thereafter, the medium was changed to RPMI medium (containing 10% by volume FBS), followed by culture for 48 hours. The culture using RPMI medium (containing 10% by volume FBS) had the medium replaced with a fresh medium at 24 hours after the start of culture. The area of wound area was determined at 0, 24 and 48 hours from the start of culture using RPMI medium (containing 10% by volume FBS). When the wound area at 0 hour from the start of culture was 100%, the percentages of wound area at 24 and 48 hours after culture were determined. In addition, tests were also performed under the same condition on a case where a control miRNA (SEQ ID NO: 9) was used (control miRNA, negative control) in place of hsa-miR-3065-3p.

Figure 17:
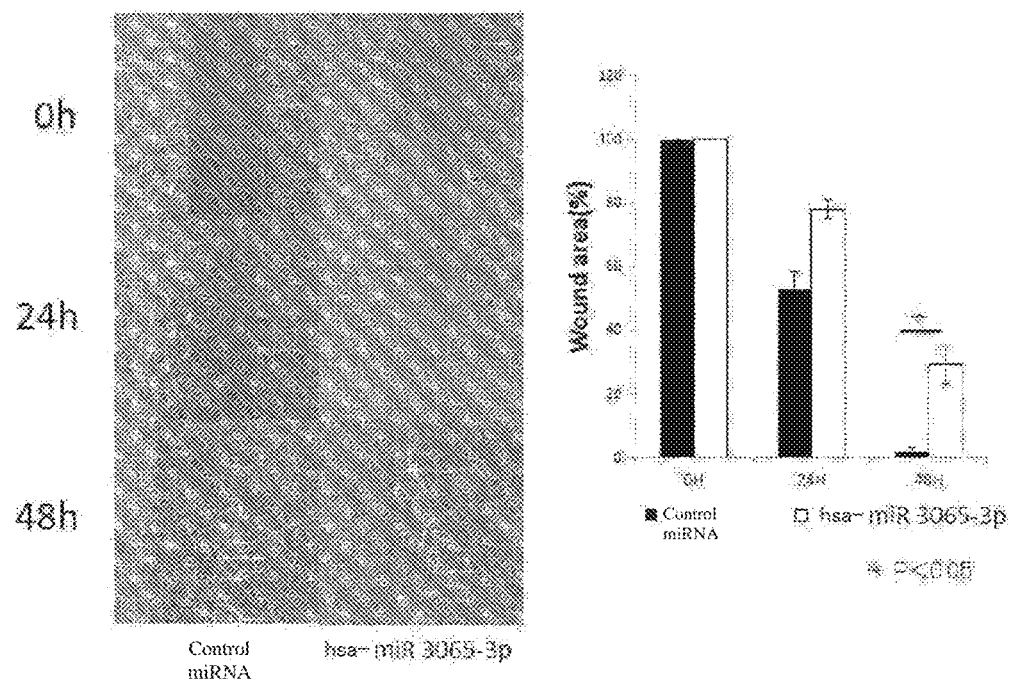
FIG. 17 is the result of wound healing assay performed using hsa-miR-3065-3p and human large bowel cancer cells.

The obtained result is shown in FIG. 17. From the result, in human large bowel cancer cells treated with hsa-miR-3065-3p, the decrease in wound area was significantly suppressed as compared to the negative control. In other words, from the result, it has been clear that hsa-miR-3065-3p is able to suppress migration of human large bowel cancer cells.

The invention claimed is:

1. A method of inhibiting proliferation of a cancer stem cell, the method comprising administering to the cancer stem cell:
   (a) at least one miRNA as an active ingredient, wherein the at least one miRNA is:
      (1) hsa miR-136-5p, hsa-miR-3065-3p, hsa-miR-4727-5p, hsa-miR-378g and/or hsa-miR-181a-5p delivered to pancreatic tumor cells;
      (2) hsa-miR-136-5p, hsa-miR-3065-3p, and/or hsa-miR-181a-5p delivered to gastric tumor cells;
      (3) hsa-miR-136-5p, hsa-miR-3065-3p, hsa-miR-4727-5p, hsa-miR-378g, hsa-miR-181a-5p, hsa-miR-362-5p, and/or hsa-miR-608 delivered to human large bowel cancer cells; or
      (4) hsa-miR-136-5p, hsa-miR-3065-3p, hsa-miR-4727-5p, hsa-miR-378g, and/or hsa-miR-181a-5p delivered to esophageal cancer cells; and
   (b) an miRNA transfer agent;
   wherein the at least one miRNA and the miRNA transfer agent are administered simultaneously with an anticancer drug, or before and/or after administration of an anticancer drug.

2. The method according to claim 1, wherein the miRNA is a mature miRNA, pri-miRNA or pre-miRNA.

3. The method according to claim 1, wherein the miRNA transfer agent comprises carbonate apatite particles and the at least one miRNA is complexed to the carbonate apatite particles.

4. A method for treating cancer, comprising a step of administering to a cancer patient a therapeutically effective amount of:
   (a) at least one miRNA, wherein the at least one miRNA is:
      (1) hsa miR-136-5p, hsa-miR-3065-3p, hsa-miR-4727-5p, hsa-miR-378g and/or hsa-miR-18 la-5p delivered to pancreatic tumor cells;
      (2) hsa-miR-136-5p, hsa-miR-3065-3p, and/or hsa-miR-181a-5p delivered to gastric tumor cells;
      (3) hsa-miR-136-5p, hsa-miR-3065-3p, hsa-miR-4727-5p, hsa-miR-378g, hsa-miR-181a-5p, hsa-miR-362-5p, and/or hsa-miR-608 delivered to human large bowel cancer cells; or
      (4) hsa-miR-136-5p, hsa-miR-3065-3p, hsa-miR-4727-5p, hsa-miR-378g, and/or hsa-miR-181a-5p delivered to esophageal cancer cells; and
   (b) an miRNA transfer agent.

5. The method for treating cancer according to claim 4, wherein the miRNA is administered simultaneously with an anticancer drug, or before and/or after administration of an anticancer drug.

* * * * *

```
                           SEQUENCE LISTING

<160> NUMBER OF SEQ ID NOS: 10

<210> SEQ ID NO 1
<211> LENGTH: 23
<212> TYPE: RNA
<213> ORGANISM: Homo sapiens

<400> SEQUENCE: 1
acuccauuug uuuugaugau gga                                           23

<210> SEQ ID NO 2
<211> LENGTH: 23
<212> TYPE: RNA
<213> ORGANISM: Homo sapiens

<400> SEQUENCE: 2
ucagcaccag gauauuguug gag                                           23

<210> SEQ ID NO 3
<211> LENGTH: 21
<212> TYPE: RNA
<213> ORGANISM: Homo sapiens

<400> SEQUENCE: 3
aucugccagc uuccacagug g                                             21

<210> SEQ ID NO 4
<211> LENGTH: 20
<212> TYPE: RNA
<213> ORGANISM: Homo sapiens

<400> SEQUENCE: 4
acugggcuug gagucagaag                                               20

<210> SEQ ID NO 5
<211> LENGTH: 23
<212> TYPE: RNA
<213> ORGANISM: Homo sapiens

<400> SEQUENCE: 5
aacauucaac gcugucggug agu                                           23

<210> SEQ ID NO 6
<211> LENGTH: 24
<212> TYPE: RNA
<213> ORGANISM: Homo sapiens

<400> SEQUENCE: 6
aauccuugga accuaggugu gagu                                          24
```

<210> SEQ ID NO 7
<211> LENGTH: 25
<212> TYPE: RNA
<213> ORGANISM: Homo sapiens

<400> SEQUENCE: 7 aggggguggug uugggacagc uccgu                                     25

<210> SEQ ID NO 8
<211> LENGTH: 22
<212> TYPE: RNA
<213> ORGANISM: Homo sapiens

<400> SEQUENCE: 8
uggcaguguc uuagcugguu gu                                         22

<210> SEQ ID NO 9
<211> LENGTH: 19
<212> TYPE: RNA
<213> ORGANISM: Artificial Sequence
<220> FEATURE:
<223> OTHER INFORMATION: Control miRNA

<400> SEQUENCE: 9
auccgcgcga uaguacgua                                             19

<210> SEQ ID NO 10
<211> LENGTH: 858
<212> TYPE: DNA
<213> ORGANISM: Homo sapiens

<400> SEQUENCE: 10
atggcccagt ccaagcacgg cctgaccaag gagatgacca tgaagtaccg catggagggc    60
tgcgtggatg ccacaagtt cgtgatcacc ggcgagggca tcggctaccc cttcaagggc   120
aagcaggcca tcaacctgtg cgtggtggag ggcggccect tgcccttcgc cgaggacatc   180
ttgtccgccg ccttcaacta cggcaaccgc gtgttcaccg agtaccccca ggacatcgtc   240
gactacttca agaactcctg ccccgccggc tacacctggg accgctcctt cctgttcgag   300
gacggcgccg tgtgcatctg caacgccgac atcaccgtga gcgtggagga gaactgcatg   360
taccacgagt ccaagttcta cggcgtgaac ttccccgccg acggcccgt gatgaagaag   420 atgaccgaca ctgggagcc ctcctgcgag aagatcatcc ccgtgcccaa gcagggcatc   480
ttgaagggcg acgtgagcat gtacctgctg ctgaaggacg gtggccgctt gcgctgccag   540
ttcgacaccg tgtacaaggc caagtccgtg ccccgcaaga tgcccgactg gcacttcatc   600
cagcacaagc tgacccgcga ggaccgcagc gacgccaaga accagaagtg gcacctgacc   660
gagcacgcca tcgcctccgg ctccgccttg cccccgcggt cacggccaat gtggcaactc   720
atgaaacaga tccagagcca tggcttcccg ccggaggtgg aggagcagga tgatggcacg   780
ctgcccatgt cttgtgccca ggagagcggg atggaccgtc accctgcagc ctgtgcttct   840
gctaggatca atgtgtag                                                858